United States Patent
Kotschy et al.

(10) Patent No.: US 11,332,472 B2
(45) Date of Patent: May 17, 2022

(54) SUBSTITUTED PIPERIDINES AS INHIBITORS OF UBIQUITIN SPECIFIC PROTEASE 7

(71) Applicants: LES LABORATOIRES SERVIER, Suresnes (FR); VERNALIS (R&D) LTD, Cambridge (GB)

(72) Inventors: András Kotschy, Törökbálint (HU); Csaba Wéber, Pilisszentlászló (HU); Attila Vasas, Fót (HU); Árpád Kiss, Budapest (HU); Balázs Molnár, Isaszeg (HU); Ágnes Strofek, Esztergom (HU); Vilibald Kun, Tárnok (HU); James Brooke Murray, Linton (GB); Alba Macias, Cambridgeshire (GB); Elodie Lewkowicz, Paris (FR); Maïa Chanrion, Issy les Moulineaux (FR); Lisa Ivanschitz, Massy (FR); Olivier Geneste, Rueil-Malmaison (FR)

(73) Assignees: LES LABORATOIRES SERVIER, Suresnes (FR); VERNALIS (R&D) LTD, Cambridge (GB)

( * ) Notice: Subject to any disclaimer, the term of this patent is extended or adjusted under 35 U.S.C. 154(b) by 0 days.

(21) Appl. No.: 16/764,982

(22) PCT Filed: Nov. 28, 2018

(86) PCT No.: PCT/EP2018/082766
§ 371 (c)(1),
(2) Date: May 18, 2020

(87) PCT Pub. No.: WO2019/105963
PCT Pub. Date: Jun. 6, 2019

(65) Prior Publication Data
US 2020/0407363 A1    Dec. 31, 2020

(30) Foreign Application Priority Data
Nov. 29, 2017 (FR) ...................................... 1761338

(51) Int. Cl.
*A61K 31/4523* (2006.01)
*C07D 211/48* (2006.01)
*C07D 487/04* (2006.01)
*A61K 45/06* (2006.01)

(52) U.S. Cl.
CPC ............ *C07D 487/04* (2013.01); *A61K 45/06* (2013.01)

(58) Field of Classification Search
CPC .......................... A61K 31/4523; C07D 211/48
USPC ........................................ 514/326; 546/245
See application file for complete search history.

(56) References Cited

U.S. PATENT DOCUMENTS

2016/0185785 A1   6/2016   Ioannidis
2016/0185786 A1   6/2016   Ioannidis

FOREIGN PATENT DOCUMENTS

WO   WO 2017212012   12/2017

OTHER PUBLICATIONS

Jordan, V. C. Nature Reviews: Drug Discovery, 2, 2003, 205.*
Hackam, et al. JAMA, 296(14), 2006, 1731-1732.*
International Search Report for PCT/EP2018082766 dated Jan. 29, 2019.
Agathanggelou, et al., Blood, 2017, 130(2), 156-166.
Alonso de Vega, et al., Cell Cycle, 2014, 13(24), 3921-3926.
An, et al., Biochem Pharmacol., 2017, 131, 29-39.
Cai, et al., Hepatology, 2015, 61(5), 1603-1614.
Callegari, et al., Cell Commun Signal., 2018, 16(1), 60.
Carrá, et al., Oncotarget, 2017, 8(22), 35508-35522.
Chauhan, et al., Cancer Cell, 2012, 22, 345-358.
Chen, et al., J Biol Chem., 2015, 290(35), 21713-21723.
Cheng, et al., Nat. Commun., 2015, 6, 7023.
Cheng, et al., Oncol Rep., 2013, 29(5), 1730-1736.
Cummins, et al., Cell Cycle, 2004, 3(6), 689-692.
Felle, et al., Nucleic Acids Res., 2011, 39(19), 8355-8365.
Franqui-Machin, et al., J Clin Invest., 2018, 128(7), 2877-2893.
Fu, et al., Onco Targets Ther., 2019, 12, 609-617.
He, et al., J Biol Chem., 2019, pii: jbc.RA119.010724.
Hernández-Pérez, et al., Oncogene, 2017, 36(33), 4802-4809.
Hu, et al., Mol Carcinog., 2019, 58(1), 42-54.
Jin, et al., Clin Cancer Res., 2019, 25(1), 222-239.
Li, et al., Mol Cell, 2004, 13(6), 879-886.
Li, et al., Nature, 2002, 416(6881), 648-653.
Liu, et al., EMBO Rep., 2019, e48597.
Ma, et al., Onco Targets Ther., 2016, 9, 1559-1569.
Malapelle, et al., Lung Cancer, 2017, 107, 41-49.
Masuya, et al., J Pathol., 2006, 208(5), 724-732.
Morotti, et al., Eur J Haematol., 2015, 94(4), 318-321.
Morra, et al., J Exp Clin Cancer Res., 2019, 38(1), 90.
Morra, et al., Oncotarget, 2015, 6(14), 12697-12709.
Morra, et al., Oncotarget, 2017, 8(19), 31815-31829.

(Continued)

Primary Examiner — Douglas M Willis
(74) Attorney, Agent, or Firm — Hueschen and Sage

(57) ABSTRACT

Compounds of formula (I):

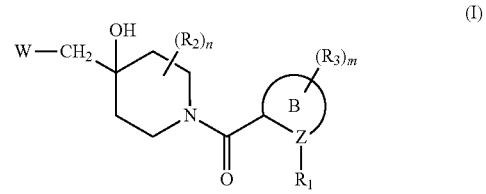

wherein $R_1$, $R_2$, $R_3$, B, W, Z, m and n are as defined in the description.

12 Claims, No Drawings

(56) References Cited

OTHER PUBLICATIONS

Noguera, et al., Leukemia, 2013, 27(5), 1037-1043.
Novellasdemunt, et al., Cell Rep., 2017, 21(3), 612-627.
Qin, et al., J Cell Biochem., 2011, 112(2), 439-444.
Qin, et al., Oncotarget, 2016, 7(47), 77096-77109.
Shan, et al., Signal Transduct Target Ther., 2018, 3, 29.
Sho, et al., J Surg Oncol., 2017, 116(8), 996-1004.
Song, et al., Nature, 2008, 455, 813-817.
Su, et al., J Clin Invest., 2018, 128(10), 4280-4296.
Sun, et al., Nat Commun., 2019, 10(1), 411.
Tavana, et al., Nat Med., 2016, 22(10), 1180-1186.
Van der Knapp, et al., Molecular Cell, vol. 17, Mar. 4, 2005, 695-707.
Van Loosdregt, et al., Immunity, 2013, 39, 259-271.
Varol, et al., Exp Biol Med, 2015, 240(5), 624-630.
Vishnoi, et al., Cancer Res. 2018, 78(18), 5349-5362.
Wang, et al., Cell Physiol Biochem., 2017, 43(5), 1755-1766.
Wang, et al., EBioMedicine, 2016, 13, 99-112.
Wang, et al., J. Clin. Invest., 2016, 126(6), 2205-2220.
Wang, et al., Med Sci Monit., 2018, 24, 1742-1750.
Wang, et al., PLoS One, 2017, 12(12), e0189744.
Xia, et al., Cancer Lett., 2019, 465, 118-128.
Xia, et al., Mol Oncol., 2020, doi: 10.1002/1878-0261.12641.
Yamaguchi, et al., Sci Rep. 2017, 7(1), 55.
Yao, et al., J Leukoc Biol., 2018, 104(6), 1105-1115.
Zhang, et al., Int J Biochem Cell Biol., 2016, 79, 209-221.
Zhang, et al., Nat Cell Biol., 2014, 16(9), 864-875.
Zhang, et al., Tohoku J Exp. Med., 2016, 239(3), 165-175.
Zhao, et al., Tumor Biol., 2015, 36, 1721-1729.
Zhu, et al., Cell Cycle, 2015, 14(9), 1413-1425.
Zlatanou, et al., Oncogene, 2016, 35(8), 965-976.

* cited by examiner

SUBSTITUTED PIPERIDINES AS INHIBITORS OF UBIQUITIN SPECIFIC PROTEASE 7

The present invention relates to new piperidinyl derivatives, to a process for their preparation and to pharmaceutical compositions containing them.

The compounds of the present invention are new and have very valuable pharmacological characteristics in the field of apoptosis and oncology.

Ubiquitination is a process controlling essential cellular functions such as protein turnover and homeostasis, protein activation and localisation. Ubiquitin is a 76 amino acids polypeptide which is covalently attached to postranslationnaly modified protein substrates via an isopeptide bond. Deubiquinating enzymes (DUBs) are in majority cysteine proteases that cleave the ubiquitin-ubiquitin bond or ubiquitin-protein bond at the Cter glycine of Ubiquitin. Approximately 100 DUBs regulate the thousands ubiquitinated proteins and then some redundancy of deubiquitinase substrates regulation are observed.

Dysregulation of DUBs have been associated with several diseases such as neurodegenerative and infectious diseases (Edelman et. al., *Expert Rev. Mol. Med.* 2011, 13, 1-17) and human malignancies (Pal et. al., *Cancer Rev.* 2014.74, 4953-4966). Accordingly, overexpression of DUBs or increase of their activity have been associated to numerous types of cancers (Luise et. al., Plos One 2011, 6, e15891: Rolen et. al., *Mol. Carcinog.* 2006, 45, 260-269) and poor prognosis.

Ubiquitin Specific Protease 7 (USP7), also known as Herpes-virus-Associated Ubiquitin-Specific Protease (HAUSP), belongs to the deubiquitinating family. USP7 has been reported to stabilize numerous oncogenes involved in survival and proliferations via cell cycle progression, apoptosis, DNA repair. DNA replication and epigenetic factors regulation (Nicholson et al., *Cell Biochem. Biophys.* 2011, 60, 61-68). In addition. USP7 has been shown to regulate immune response via inflammation and Treg modulation (Van Loosdregt et. al., Immunity 2013, 39, 259-27; Colleran et. al., *Proc. Natl. Acad. Sci. USA* 2013, 110.618-623). USP7 has also been implicated in other pathologic states such as neurodevelopmental disorder (Hao et. al., *Mol. Cell* 2015, 59, 956-96) and viral infection (Holowaty et. al., *Biochem. Soc. Trans.* 2004, 32, 731-732).

USP7 overexpression has been associated with late stages of cancers and poor prognosis in lung, neuroblastoma, myeloma, prostate, colon and breast cancers. Numerous USP7 inhibitors have been recently published in the literature (Turnbull et. al., *Nature* 2017, 550, 481-416: Kategaya et. al. *Nature* 2017, 551), 534-538: Gavory et. al., *Nat. Chem. Biol.* 2018. 14, 118-125: O'Dowd et. al., *ACS Med. Chem. Lett.* 2018, 9, 238-243; Pozhidaeva et. al., *Cell Chem Biol.* 2017, 24, 1501-1512. Lamberto et. al., *Cell Chem. Biol* 2017, 24, 1490-1500; US 2016; 185785; US 2016/185786). Despite an intense research in the field, no USP7 inhibitors have entered the clinic (Kemp et. al., *Progress in Medicinal Chemistry* 2016, 55, 149-192). There is, therefore, a therapeutic need for compounds that inhibit the activity of the protein USP7.

In addition to being new, the compounds of the present invention have pro-apoptotic and/or anti-proliferative properties making it possible to use them in pathologies involving a defect in apoptosis, such as, for example, in the treatment of cancer and of immune and auto-immune diseases.

The present invention relates more especially to compounds of formula ii):

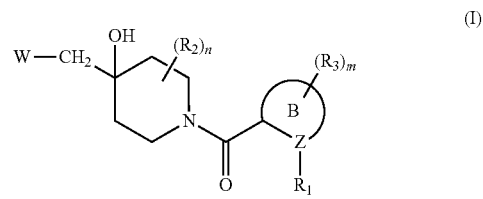

wherein:
$R_1$ represents a cycloalkyl group, a heterocycloalkyl group, an aryl group, or a heteroaryl group,
$R_2$ represents a hydrogen atom or a halogen atom,
$R_3$ represents a hydrogen atom, a halogen atom, a linear or branched $(C_1-C_6)$alkyl group, a hydroxy group or an oxo group,
n and m, independently of one another, are an integer equal to 0, 1 or 2.,
B represents a cycloalkyl ring or a heterocycloalkyl ring,
Z represents a carbon atom or a nitrogen atom,
W represents the group

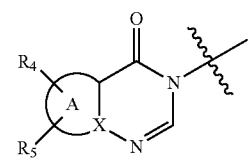

wherein,
A represents a heteroaryl ring,
X represents a carbon atom or a nitrogen atom,
$R_4$ represents a hydrogen atom, a halogen atom, a linear or branched $(C_1-C_6)$alkyl group, a linear or branched $(C_2-C_6)$alkenyl group, a linear or branched $(C_2-C_6)$alkynyl group, a $-Y_1-NR_6R_7$ group, a $-Y_1-OR_6$ group, a linear or branched halo$(C_1-C_6)$alkyl group, an oxo group, a $-Y_1-Cy_1$ group, a $-Cy_1-R_2$ group, a $-Cy_1-OR_7$ group, or a $-Y_1-NR_6-C(O)-R_7$ group,
$R_5$ represents a hydrogen atom, a halogen atom, a linear or branched $(C_1-C_6)$alkyl group, a cyano group, or a -hydroxy$(C_1-C_6)$alkyl group,
$R_6$ represents a hydrogen atom or a linear or branched $(C_1-C_6)$alkyl group,
$R_7$ represents a hydrogen atom, a linear or branched $(C_1-C_6)$alkyl group, a $-Y_2-Cy_2$ group, or a $-Y_2-SR_x$ group,
$Y_1$ and $Y_2$ independently of one another represent a bond or a linear or branched $(C_1-C_4)$alkylene group,
$R_8$ represents a hydrogen atom, or a linear or branched $(C_1-C_6)$alkyl group,
$Cy_1$ and $Cy_2$ independently of one another, represent a cycloalkyl group, a heterocycloalkyl group, an aryl group, or a heteroaryl group,
it being understood that:
"aryl" means a phenyl, naphthyl, or indanyl group,
"heteroaryl" means any mono- or fused bi-cyclic group composed of from 5 to 10 ring members, having at least one aromatic moiety and containing from 1 to 3 heteroatoms selected from oxygen, sulphur and nitrogen, "cycloalkyl" means any mono- or fused bi-cyclic non-aromatic carbocyclic group containing from 3 to 7 ring members, "heterocycloalkyl" means any non-aromatic mono- or fused bi-cyclic group containing from 3 to 10 ring members, and containing from 1 to 3 heteroatoms selected from oxygen, sulphur and nitrogen, it being possible for the aryl, heteroaryl, cycloalkyl and heterocycloalkyl groups so defined to be substituted by from 1 to 4 groups selected from linear or branched $(C_1$-$C_6)$alkyl, linear or branched $(C_2$-$C_6)$alkenyl, linear or branched $(C_2$-$C_6)$alkynyl, linear or branched halo$(C_1$-$C_6)$alkyl, —$Y_1$—OR', —$Y_1$—NR'R", —$Y_1$—S(O)$_m$—R', oxo (or N-oxide where appropriate), nitro, cyano, —C(O)—R', —C(O)—OR', —O—C(O)—R', —C(O)—NR'R", —$Y_1$—NR'—C(O)—R", —$Y_1$—NR'—C(O)—OR", halogen, cyclopropyl, and pyridinyl which can be substituted by a linear or branched $(C_1$-$C_6)$alkyl group, it being understood that R' and R" independently of one another represent a hydrogen atom, a linear or branched $(C_1$-$C_6)$alkyl group, a linear or branched $(C_2$-$C_6)$alkenyl group, a linear or branched $(C_1$-$C_6)$alkoxy group, a linear or branched halo$(C_1$-$C_6)$alkyl, a linear or branched hydroxy $(C_1$-$C_6)$alkyl group, a linear or branched $(C_1$-$C_6)$alkoxy$(C_1$-$C_6)$alkyl group, a phenyl group, a cyclopropylmethyl group, a tetrahydropyranyl group, or the substituents of the pair (R', R") form together with the nitrogen atom carrying them a non-aromatic ring composed of from 5 to 7 ring members, which may contain in addition to the nitrogen a second heteroatom selected from oxygen and nitrogen, it being understood that the nitrogen in question may be substituted by from 1 to 2 groups representing a hydrogen atom, or a linear or branched $(C_1$-$C_6)$alkyl group, and it being understood that m is an integer equal to 0, 1 and 2, their enantiomers, diastereoisomers, and addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable base there may be mentioned, without implying any limitation, sodium hydroxide, potassium hydroxide, triethylamine, tert-butylamine etc.

Among the heteroaryl groups there may be mentioned, without implying any limitation, pyrrolyl, furyl, thienyl, thiazolyl, isothiazolyl, oxazolyl, isoxazolyl, pyrazolyl, imidazolyl, pyridinyl, pyrazinyl, pyridazinyl, pyrimidinyl, pyridinonyl, indolyl, dihydroindolyl, dihydroisoindolyl, indazolyl, dihydrocyclopentathienyl, benzothienyl, tetrahydrobenzotheinyl, benzofuranyl, imidazopyridinyl, benzotriazolyl, benzodioxolyl, dihydrobenzodioxinyl, quinolinyl, isoquinolinyl, tetrahydroquinolinyl, tetrahydroisoquinolinyl, quinoxalinyl, dihydroquinoxalinyl, dihydrothienodioxinyl, quinazolinonyl, pyrrolopyridazinyl, dihydropyrrolizinyl, tetrahydroindolizinyl, etc.

Among the cycloalkyl groups there may be mentioned, without implying any limitation, cyclopropyl, cyclobutyl, cyclopentyl, cyclohexyl, etc.

Among the heterocycloalkyl groups there may be mentioned, without implying any limitation, pyrrolidinyl, tetrahydropyranyl, piperidinyl, piperazinyl, morpholinyl, etc.

In another embodiment of the invention, W advantageously represents the group

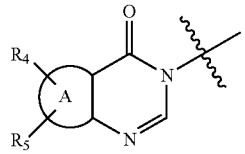

wherein $R_4$, $R_5$ and A are as defined for formula (I),

More especially,

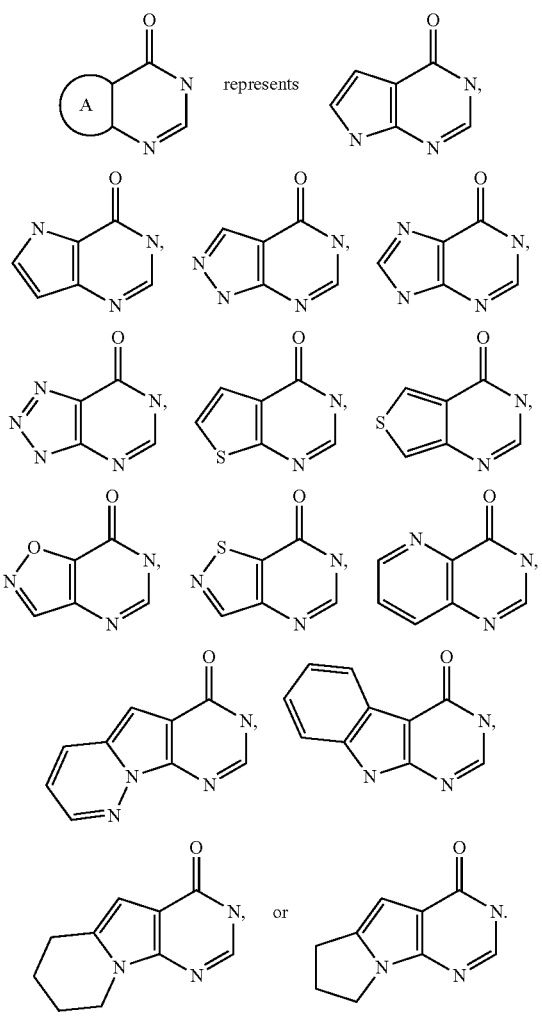

More particularly,

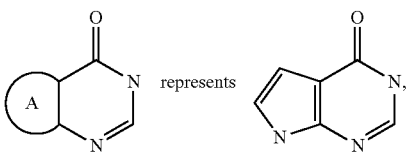

-continued

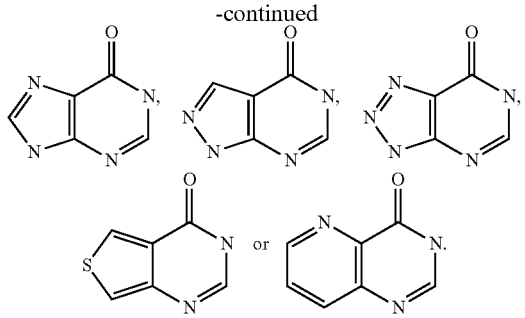

Advantageously,

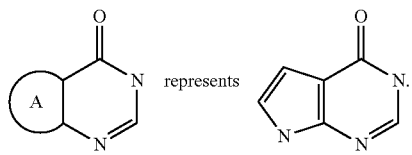 represents

In another embodiment of the invention, an advantageous possibility consists of compounds of Formula (I-a):

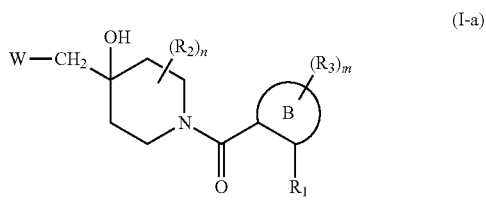

wherein $R_1$, $R_2$, $R_3$, W, m and n are as defined in formula (I).
Preferably, the fragment

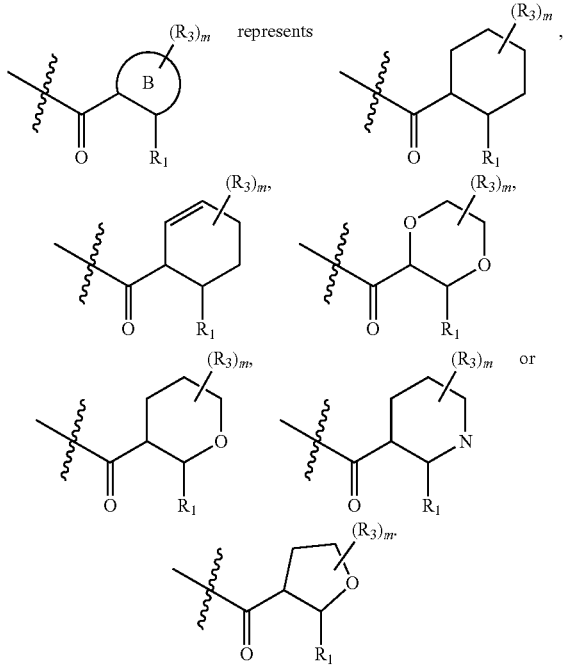

More preferably, the fragment

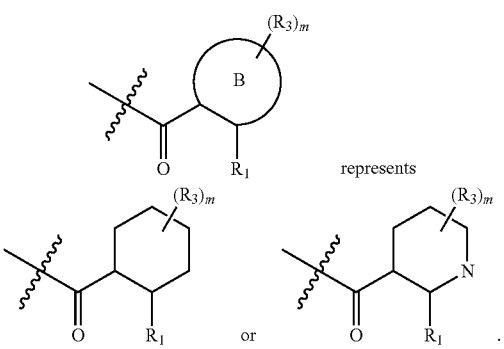 represents

In another embodiment of the invention, an advantageous possibility consists of compounds of formula (I-b):

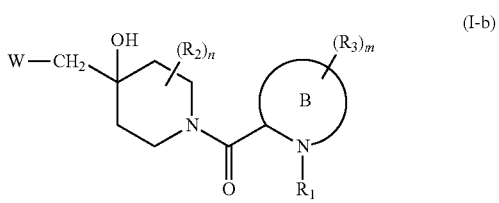

wherein $R_1$, $R_2$, $R_3$, W, m and n are as defined in formula (I)
Preferably, the fragment

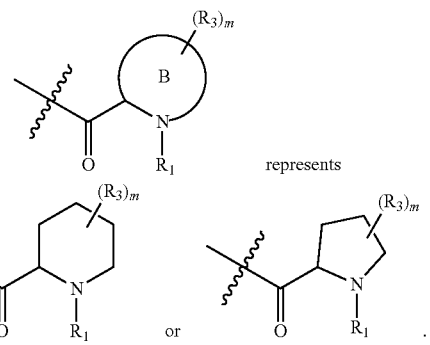 represents

Advantageously, the compounds of formula (I-a) displays a trans configuration as follows:

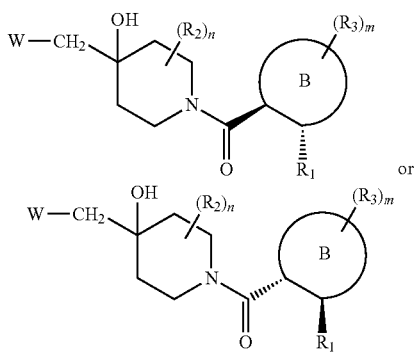

$R_1$ advantageously represents a phenyl group, a furyl group, a pyrrolyl group, a thienyl group, an imidazolyl group, a pyrazolyl group, a triazolyl group, an oxazolyl group, a thiazolyl group, a pyridinyl group or a pyrrolidinyl group. More preferably, $R_1$ represents a phenyl group, a furyl group or a pyrrolyl group.

$R_2$ preferably represents a hydrogen atom or a fluorine atom. More preferably, $R_2$ represents a hydrogen atom.

$R_3$ preferably represents a hydrogen atom, a fluorine atom, a hydroxy group, an oxo group or a methyl group. More preferably, $R_3$ represents a hydrogen atom, a fluorine atom, an oxo group or a methyl group. Advantageously, the $-(R_3)_m$ group represents a gem-difluoro group.

Advantageously, $R_4$ represents a hydrogen atom, a halogen atom, a linear or branched $(C_1-C_6)$alkyl group, a $-Y_1-NR_6R_7$, group, a $-Y_1$-$Cy_1$ group, or a $-Y_1-NR_6-C(O)-R_7$ group. More preferably, $R_4$ represents a $-Y_1$-$Cy_1$ group. Even more preferably. $R_4$ represents a phenyl group.

$R_5$ and $R_6$ preferably represent a hydrogen atom.

$R_7$ represents a hydrogen atom, a $-Y_2$-$Cy_2$ group or a $-Y_2-SR_8$ group.

Among the preferred compounds of the invention there may be mentioned:

- 3-[[4-hydroxy-1-[trans-2-pyrrol-1-ylcyclohexanecarbonyl]-4-piperidyl]methyl]-7-phenyl-pyrrolo[2,3-d]pyrimidin-4-one;
- 3-[[4-hydroxy-1-[trans-2-pyrrol-1-ylcyclohexanecarbonyl]-4-piperidyl]methyl]-7-(4-methoxyphenyl)pyrrolo[2,3-d]pyrimidin-4-one;
- 3-[[4-hydroxy-1-[(trans-1-methyl-6-oxo-2-phenyl-piperidine-3-carbonyl]-4-piperidyl]methyl]-7-phenyl-pyrrolo[2,3-d]pyrimidin-4-one;
- 3-[[1-[trans-5,5-difluoro-2-phenyl-cyclohexanecarbonyl]-4-hydroxy-4-piperidyl]methyl]-7-(4-methoxyphenyl)pyrrolo[2,3-d]pyrimidin-4-one;
- 3-[[1-[trans-5,5-difluoro-2-phenyl-cyclohexanecarbonyl]-4-hydroxy-4-piperidyl]methyl]-7-phenyl-pyrrolo[2,3-d]pyrimidin-4-one;
- 3-[[1-[trans-4,4-difluoro-2-phenyl-cyclohexanecarbonyl]-4-hydroxy-4-piperidyl]methyl]-7-(4-methoxyphenyl)pyrrolo[2,3-d]pyrimidin-4-one;
- 3-[[1-[trans-4,4-difluoro-2-(3-furyl)cyclohexanecarbonyl]-4-hydroxy-4-piperidyl]methyl]-7-(4-methoxyphenyl)pyrrolo[2,3-d]pyrimidin-4-one.

The invention relates also to a process for the preparation of compounds of formula (I), which process is characterized in that there is used as starting material the compound of formula (II):

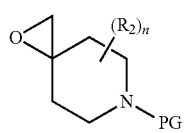

(II)

wherein $R_2$ and n are as defined for formula (I) and PG represents a protecting group of the amine function, which is subjected, after removing the protecting group of the amine function, to coupling with a compound of formula (III):

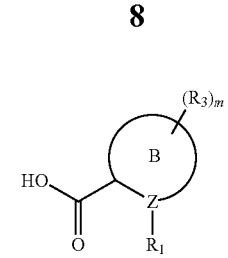

(III)

wherein $R_1$, $R_3$, B, Z and m are as defined for formula (I), to yield the compound of formula (IV):

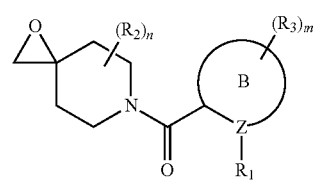

(IV)

wherein $R_1$, $R_2$, $R_3$, B, Z, m and n are as defined hereinbefore, compound of formula (IV) which is further subjected to coupling with compound of formula (V):

(V)

wherein W is as defined for formula (I), to yield the compound of formula (I), which may then be purified according to a conventional separation technique, which is converted, if desired, into its addition salts with a pharmaceutically acceptable acid or base and which is optionally separated into its isomers according to a conventional separation technique, it being understood that at any moment considered appropriate during the course of the process described above, some groups (hydroxy, amino . . . ) of the starting reagents or of the synthesis intermediates can be protected, subsequently deprotected and functionalized, as required by the synthesis.

In another embodiment of the invention, compounds of formula (I) may be obtained using an alternative process, which process is characterised in that there is used as starting material the compound of formula (II):

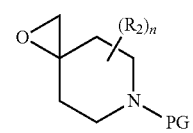

(II)

wherein $R_2$ and n are as defined for formula (I) and PG represents a protecting group of the amine function, which is subjected to coupling with compound of formula (V):

(V)

wherein W is as defined for formula (I), to yield the compound of formula (VI):

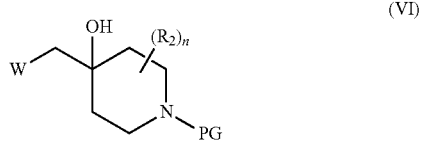

wherein $R_2$, W, PG and n are as defined hereinbefore, which is further subjected, after removing the protecting group of the amine function, to coupling with a compound of formula (III):

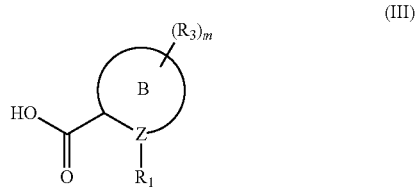

wherein $R_1$, $R_3$, B, Z and in are as defined for formula (I), to yield the compound of formula (I), which may then be purified according to a conventional separation technique, which is converted, if desired, into its addition salts with a pharmaceutically acceptable acid or base and which is optionally separated into its isomers according to a conventional separation technique, it being understood that at any moment considered appropriate during the course of the process described above, some groups (hydroxy, amino . . . ) of the starting reagents or of the synthesis intermediates can be protected, subsequently deprotected and functionalized, as required by the synthesis.

The compounds of formulae (II). (III) and (V) are either commercially available or can be obtained by the person skilled in the art using conventional chemical reactions described in the literature.

Pharmacological studies of the compounds of the invention have shown pro-apoptotic and/or anti-proliferative properties. The ability to reactivate the apoptotic process in cancerous cells is of major therapeutic interest in the treatment of cancers and of immune and auto-immune diseases.

Among the cancer treatments envisaged there may be mentioned, without implying any limitation, treatment of cancers of the bladder, brain, breast and uterus, chronic lymphoid leukemia, cancer of the colon, esophagus and liver, lymphoblastic leukemia, acute myeloid leukemia, lymphomas, melanomas, malignant haemopathies, myelomas, ovarian cancer, non-small-cell lung cancer, prostate cancer, pancreatic cancer and small-cell lung cancer. More especially, the compounds according to the invention will be useful in the treatment of chemo-, targeted therapy- or radio-resistant cancers.

The present invention relates also to pharmaceutical compositions comprising at least one compound of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the combination of a compound of formula (I) with anti-cancer agents selected from genotoxic agents, mitotic poisons, anti-metabolites, proteasome inhibitors, kinase inhibitors, protein-protein interaction inhibitors, immunomodulators, E3 ligase inhibitors, chimeric antigen receptor T-cell therapy and antibodies, and also to pharmaceutical compositions comprising that type of combination and their use in the manufacture of medicaments for use in the treatment of cancer.

The combination of a compound of formula (I) with an anticancer agent may be administered simultaneously or sequentially. The administration route is preferably the oral route, and the corresponding pharmaceutical compositions may allow the instantaneous or delayed release of the active ingredients. The compounds of the combination may moreover be administered in the form of two separate pharmaceutical compositions, each containing one of the active ingredients, or in the form of a single pharmaceutical composition, in which the active ingredients are in admixture.

The compounds of formula (I) may also be used in combination with radiotherapy in the treatment of cancer.

General Procedures

All reagents obtained from commercial sources were used without further purification. Anhydrous solvents were obtained from commercial sources and used without further drying.

Flash chromatography was performed on ISCO Combi-Flash Rf 200i with pre-packed silica-gel cartridges (Redisep® $R_f$ Gold High Performance).

Thin layer chromatography was conducted with 5×10 cm plates coated with Merck Type 60 $F_{254}$ silica-gel.

Microwave heating was performed in an Anton Parr MonoWave or CEM Discover® instrument.

Preparative HPLC purifications were performed on an HANBON NP7000 Liquid Chromatography system with a Gemini-NX® 5 μm C18, 250 mm×50 mm i.d. column running at a low rate of 99.9 mL×min$^{-1}$ with UV diode array detection (210-400 nm) using 5 mM aqueous $NH_4HCO_3$ solution and MeCN as eluents unless specified otherwise.

Chiral Chromatography was performed on Daicel columns in the mixture of heptane and alcohols.

Analytical LC-MS: The compounds of the present invention were characterized by high performance liquid chromatography-mass spectroscopy (HPLC-MS) on Agilent HP1200 with Agilent 6140 quadrupole LC/MS, operating in positive or negative ion electrospray ionisation mode. Molecular weight scan range is 100 to 1350. Parallel UV detection was done at 210 nm and 254 nm. Samples were supplied as a 1 mM solution in acetonitrile, or in TH/$H_2O$ (1:1) with 5 μL loop injection. LCMS analyses were performed on two instruments, one of which was operated with basic, and the other with acidic eluents. Basic LCMS: Gemini-NX, 3 μm. C18, 50 mm×3.00 mm i.d. column at 23° C., at a flow rate of 1 mL min$^{-1}$ using 5 mM ammonium bicarbonate (Solvent A) and acetonitrile (Solvent B) with a gradient starting from 100% Solvent A and finishing at 100% Solvent B over various/certain duration of time.

Acidic LCMS: ZORBAX Eclipse XDB-C18, 1.8 μm, 50 mm×4.6 mm i.d. column at 40° C. at a flow rate of 1 mL min$^{-1}$ using 0.02% v/v aqueous formic acid (Solvent A) and 0.02% v/v formic acid in acetonitrile (Solvent B) with a gradient starting from 100% Solvent A and finishing at 100% Solvent B over various/certain duration of time.

$^1$H-NMR measurements were performed on Bruker Avance III 500 MHz spectrometer and Bruker Avance III 400 MHz spectrometer, using DMSO-d or CDCl$_3$ as solvent. $^1$H NMR data is in the form of delta values, given in part per million (ppm), using the residual peak of the solvent (2.50 ppm for DMSO-d$_6$ and 7.26 ppm for CDCl$_3$) as internal standard. Splitting patterns are designated as: s (singlet), d (doublet), t (triplet), q (quartet), quint (quintet), sept (septet), m (multiplet), brs (broad singlet), brd (broad doublet), brt (broad triplet), brq (broad quartet), brm (broad multiplet), vbrs (very broad singlet), dd (doublet of doublets), td (triplet of doublets), di (doublet of triplets), dq (doublet of quartet), ddd (doublet of doublet of doublets), dm (doublet of multiplets), tm (triplet of multiplets), qm (quartet of multiplets).

Combination gas chromatography and low resolution mass spectrometry were performed on Agilent n gas chromatograph and Agilent 5975C mass spectrometer using 15 m×0.25 mm column with 0.25 μm HP-SMS coating and helium as carrier gas. Ion source: EI$^+$. 70 eV, 230° C., quadrupole: 150° C., interface: 34M°) C.

High resolution mass spectrometry was performed on JEOL AccuTOF MS instrument connected to Agilent 7693A gas chromatograph on Rxi-5Sil MS column 15 m×0.25 mm column and helium was used as carrier gas. Ion source: EI+, 70 eV, 200° C. interface: 250° C.

HRMS were determined on a Shimadzu IT-TOF, ion source temperature 200° C. ESI+/−, ionization voltage: (+−)4.5 kV. Mass resolution min. 10000.

Elementary analyses were performed on a Thermo Flash EA 1112 Elemental Analyzer.

List of abbreviations

| Abbreviation | Name |
|---|---|
| abs. | absolute |
| aq. | aqueous |
| Ar | Argon |
| AtaPhos | bis(di-tert-butyl(4-dimethylaminophenyl)phosphine) dichloropalladium(II) |
| Boc | tert-butoxycarbonyl |
| cc. | concentrated |
| Cs$_2$CO$_3$ | cesium carbonate |
| DAST | diethylaminosulfur trifluoride |
| DBU | 1,8-diazabicyclo[5.4.0]undec-7-ene |
| DCM | methylene chloride |
| DEE | diethylether |
| DIPO | diisopropyl oxide |
| disp. | Dispersion |
| DMEDA | N,N'-dimethylethylenediamine |
| DMF | dimethylformamide |
| DMSO | dimethylsulfoxide |
| EDC•HCl | N-(3-diniethylaminopropyl)-N'-ethylcarbodiimide hydrochloride |
| EEO | ethyl ethanoate |
| eq. | equivalent |
| HBTU | 3-[bis(dimethylamino)methyliumyl]-3H-benzotriazol-1-oxide hexafluorophosphate |
| LC | liquid chromatography |
| MeCN | acetonitrile |
| MSM | methylsulfinylmethane |
| MTBE | tert-butyl melhylether |
| PDO | p-dioxane |

List of abbreviations

| Abbreviation | Name |
|---|---|
| r.t. | room temperature |
| sat. | saturated |
| TFA | trifluoroacetic acid |
| TCEP | tris(2-carboxyethyl)phosphine |
| THF | tetrahydrofurane |
| TMSOTf | trimethylsilyl triflate |
| TMSCl | chlorotrimethylsilane |

General Procedure 1

Step 1

Preparation R1b (746 mg, 5 mmol, 1 eq.), heteroaryl/aryl-iodide (10 mmol). CuI (286 mg, 1.5 mmol, 0.3 eq.), R,R-diaminocyclohexane (171 mg, 1.5 mmol, 0.3 eq.), anhydrous K$_3$PO$_4$ (4.24 g, 20 mmol, 4 eq.) was stirred in diglyme (15 ml) for 6-16 hours at 120° C. under N$_2$ atmosphere.

Work-Up 1:

After the reaction completed, the mixture was diluted with water (200 ml)(or 25% aq. NH$_3$) and cooled to r.t. The mixture was filtered, washed with water (3×30 ml), aq. NH t solution (40 ml, 25%), water (3×50 ml), heptane (50 then 30 ml) and dried in vacuum.

Work-Up 2:

The reaction mixture was evaporated to Celite and purified by flash chromatography (heptane: EEO, gradient).

Step 2

The corresponding 4-methoxy-7-heteroaryl/aryl-pyrrolo [2,3-d]pyrimidine obtained in Step 1 above (61.3 mmol, 1 eq.), cc. HCl aqueous solution (10 ml, ~12.2 M, 122.5 mmol, 2.25 eq.) and PDO (70 ml) was stirred at 100° C. for 0.5-2 hours. After the reaction completed, the mixture was partially evaporated. The formed suspension was filtered and the solid on the filter was washed with water and dried.

General Procedure 2

Step 1

To a stirred solution of 4-chloro-7H-pyrrolo[2,3-d]pyrimidine (Preparation R1a, 1.84 g, 12 mmol, 1 eq.) in abs. DMF (15 ml), sodium-hydride (720 mg, 60% disp. in mineral oil, 18 mmol, 1.5 eq.) was added and stirred for 10 minutes at r.t. under Ar. Alkylating agent (13.2 mmol) was added to the reaction mixture and stirred for 1-6 hours at r.t. The mixture was poured into water (150 ml), then it was extracted with EEO (3×150 ml). The combined organic layers were washed with water, brine, dried over MgSO$_4$, and evaporated.

Step 2

A part of the compound obtained in Step 1 above (1.36 mmol) and lithium-hydroxide monohydrate (571 mg, 13.62 mmol, 10 eq.) were stirred in PDO-water (40 ml, 1:1 v/v) mixture at 110° C. for 7-36 hours. The reaction mixture was neutralized with 1N aq. HCl solution and the resulted precipitate was filtered off, washed with water and dried.

General Procedure 3

Step 1

Pyrimidine-4-one derivative (1 mmol), tert-butyl 1-oxa-6-azaspiro[2.5]octane-6-carboxylate (213.3 mg, 1 mmol) and $K_2CO_3$ (276.4 mg, 2 mmol, 2 eq.) were stirred in DMF (2-5 ml) at 75° C. for 2-8 hours.
Work-Up 1:
The mixture was poured into ice-water mixture and the resulted precipitate was filtered off, washed with water and dried.
Work-Up 2:
The reaction mixture was filtered and the solid was washed with DMF. The resulted filtrate was purified by preparative LC Ion C-18 Gemini-NX 5 µm column, 5 mM aqueous $NH_4HCO_3$-MeCN, gradient).

Step 2

A part of the compound obtained in Step 1 above (1 mmol) was stirred in aq. HCl solution (1N, 10 ml, 10 mmol, 10 eq.) and PDO (5 ml) for 1-3 hours at 75° C.
Work-Up 1:
The mixture was cooled to about 0-5° C. with ice bath and the white precipitate was filtered off and dried in vacuum (resulted HCl salt).
Work-Up 2:
The mixture was totally evaporated and was used to the further step (resulted HCl salt).

Step 3

Compound obtained in Step 2 above (1 mmol). EDC.HCl (3 mmol) and corresponding carboxylic acid (1 mmol) were stirred in pyridine (5 ml) at r.t. for 16 hours.
Work-Up 1:
The reaction mixture was evaporated, the residue was dissolved in DMF and injected to preparative LC (on C-18 Gemini-NX 5 µm column, 5 mM aqueous $NH_4HCO_3$-MeCN, gradient).
Work-Up 2:
The reaction mixture was evaporated. The residue was triturated with water and the resulted solid was filtered off.

General Procedure 4

Step 1

Pyrimidine-4-one derivative (1 mmol), epoxide compound Preparation R1c (1 mmol) and $K_2CO_3$ (276.4 mg, 2 mmol, 2 eq.) were stirred in DMF (2-5 ml) at 75° C. for 2-8 hours.
Work-Up 1:
The mixture was poured into ice-water mixture and the resulted precipitate was filtered off washed with water and dried.
Work-Up 2:
The reaction mixture was filtered and the solid was washed with DMF. The resulted filtrate was purified by preparative LC (on C-18 Gemini-NX 5 µm column, 5 mM aqueous $NH_4HCO_3$-MeCN, gradient).

General Procedure 5

The corresponding halogenated component (0.15 mmol, 1 eq.), corresponding boronic acid (0.375 mmol, 2.5 eq.), ATAphos•$PdCl_2$ (10.6 mg 0.0135 mmol, 0.1 eq.). $Cs_2CO_3$ (171 mg 0.525 mmol, 3.5 eq.) was diluted with THF (2.5 ml) and water (2.5 ml). The mixture was flushed with nitrogen and stirred in microwave reactor at 110° C. for 90 minutes. The reaction mixture was injected through syringe filter to preparative LC (on C-18 Gemini-NX 5 µm column, 5 mM aqueous $NH_4HCO_3$-MeCN, gradient).

General Procedure 6

Appropriate amine (1 mmol), EDC.HCl (3 mmol) and corresponding carboxylic acid (1 mmol) were stirred in pyridine (5 ml) at r.t. for 16-20 hours.
Work-Up 1:
The reaction mixture was evaporated, the residue was taken in DMF and injected to preparative LC (on C-18 Gemini-NX 5 µm column, 5 mM aqueous $NH_4HCO_3$-MeCN, gradient).
Work-Up 2:
The reaction mixture was evaporated. The residue was triturated with water and the resulted solid was filtered off.

General Procedure 7

Step 1

Preparation R1a (460 mg, 3 mmol, 1 eq.), heteroaryl/arylboronic acid (7.5 mmol) and copper(II)-acetate (817 mg, 4.5 mmol) were stirred in pyridine (10 ml) at 50-60° C. for 16-72 hours.
Work-up 1:
The mixture was evaporated to Celite and purified by flash chromatography (heptane:EEO, gradient).
Work-Up 2:
The mixture was filtered and the resulted filtrate was purified by preparative LC (on C-18 Gemini-NX 5 µm column, 5 mM aqueous $NH_4HCO_3$-MeCN, gradient).

Step 2

The resulted compound obtained in Step 1 above (1.36 mmol) and lithium-hydroxide monohydrate (571 mg, 13.6 mmol, 10 eq.) were stirred in PDO-water (40 ml, 1:1 v/v) mixture at 110° C. for 7-24 hours. The reaction mixture was neutralized with 1N aq. HCl solution, the resulted precipitate was filtered off, washed with water, dried.

General Procedure 8

Step 1

Pyrimidine-4-one derivative (1 mmol), epoxide compound Preparation R1d (1 mmol) and $K_2CO_3$ (276.4 mg, 2 mmol, 2 eq.) were stirred in DMF (2-5 ml) at 75° C. for 2-8 hours.
Work-Up 1:
The mixture was poured into ice-water mixture and the resulted precipitate was filtered off washed with water and dried.
Work-Up 2:
The reaction mixture was filtered and the solid was washed with DMF. The resulted filtrate was purified by preparative LC Ion C-18 Gemini-NX 5 µm column, 5 mM aqueous $NH_4HCO_3$-MeCN, gradient).

General Procedure 9

Step 1

Corresponding aryl-carbaldehyde (1.0 eq.) and 1-(triphenyl-phosphanylidene)propan-2-one (1.2 eq.) were dissolved in DCM. The mixture was stirred at r.t for 1-168 hours. The solvent was evaporated. The residue was purified by flash chromatography (hexane:EEO) to give the appropriate (E)-4-(aryl)but-3-en-2-one.

Step 2

A solution of corresponding (E)-4-(aryl)but-3-en-2-one obtained in Step 1 above (2.1 eq.), triethylamine (1.5 eq.) and abs. DCM were cooled to −20° C. and TMSOTf (2.0 eq.) was added dropwise. The solution was stirred for 1 hour at this temperature. The mixture was washed with aq. NaHCO$_3$ solution (5 ml) 3 times. The organic layer was dried over MgSO$_4$, then the solvent was evaporated in reduced pressure. The residue was used without further purification.

Step 3

Corresponding (E)-((4-(aryl)buta-1,3-den-2-yl)oxy)methylsilane obtained in Step 2 above (1 eq.) and ethyl acrylate (2 eq.) were dissolved in abs. toluene. The mixture was stirred at 120° C. for 1-2 days. The solvent was evaporated. The residue was dissolved in THF/1M aq. HCl 1:1 v/v mixture and stirred for 1 hour at 25° C. Then the emulsion was diluted with DEE and washed 3 times with NaHCO$_3$ solution and with brine. The organic layer was dried over MgSO$_4$ and then the solvent was evaporated under reduced pressure. The crude product was purified by lash chromatography (hexane:EEO) to give the corresponding ethyl 2-(aryl)-4-oxocyclohexane-1-carboxylate.

Step 4

Oven-dried flask was inertized then filled with ethyl 2-(aryl)-4-oxocyclohexane-1-carboxylate obtained in Step 3 above (1.0 eq.) and abs. DCM (c=0.05M). The solution was cooled to 10° C. and DAST (5.0 eq.) was added dropwise. After that the reaction mixture was stirred for 3 hours at 25° C. The reaction mixture was quenched with aq. NaHCO$_3$ solution (25 ml), and the mixture was washed with aq. NaHCO$_3$ solution twice. The organic layer was dried over MgSO$_4$, and then the solvent was evaporated under reduced pressure. The crude product was purified by column chromatography (hexane:EEO) to give the corresponding ethyl 4,4-difluoro-2-(aryl)cyclohexane-1-carboxylate.

Step 5

The corresponding ester obtained in Step 4 above was dissolved in the mixture of ethanol and water (5:1, v/v) and lithium hydroxide hydrate (2-3 eq.) was added. It was stirred at r.t. for 44-435 hours.
Work-Up 1:
The reaction mixture was partially evaporated to water and isolated as lithium salt.
Work-Up 2:
The reaction mixture was evaporated to water, then 1N HCl was added. The obtained solid compound was filtered off.
Work-Up 3:
The reaction mixture was evaporated to water, 1N HCl was added, and then it was evaporated again. The residue was purified by preparative HPLC (on C-18 Gemini-NX 5 μm column, 5 mM aqueous NH$_4$HCO$_3$-MeCN, gradient).

Preparation R1b:
4-methoxy-7H-pyrrolo[2,3-d]pyrimidine

Preparation R1a (100 g, 0.65 mol, 1 eq.). NaOH (31.26 g, 0.78 mol, 1.2 eq.) and MeOH (400 ml) was stirred at 90° C. for 24 hours. The mixture was quenched with water (1200 ml) and cooled to r.t. with ice bath. The mixture is stirred for 30 minutes and filtered through a glass filter. The precipitate was washed with water (3×100 ml) then it was filtered off to give Preparation R1b as a white solid. HRMS calculated for $C_7H_7N_3O$: 149.0599: found 150.0667 [(M+H)$^+$ form].
$^1$H-NMR (400 MHz, MSM-d6): δ=12.02 (vbrs, 1H), 8.37 (s, 1H), 7.35 (d, 1H), 6.47 (d, 1H), 4.02 (s, 3H).
$^{13}$C-NMR (100 MHz, MSM-d6): δ ppm 162.6, 152.9, 150.8, 124.6, 104.8, 98.3, 53.7.

Preparation R1 c: 1-oxa-6-azaspiro[2.5]octan-6-yl-[trans-2-phenylcyclohexyl]methanone Step 1: 1-[trans-2-phenylcyclohexanecarbonyl]piperidin-4-one 4-Piperidone hydrochloride hydrate (2.0 g, 9.79 mmol). EDC.HCl (5.6 g, 29.4 mmol) and trans-2-phenylcyclohexanecarboxylic acid (1.5 g, 9.79 mmol) were dissolved in pyridine (90 mL) and stirred at r.t. for 23 hours. The reaction mixture was poured into water. A solid compound was formed and it was filtered off to give the product of the title.
HRMS calculated for $C_{18}H_{23}NO_2$: 285.1729. found 286.1800 [(M+H)$^+$ form].
$^1$H-NMR (500 MHz, MSM-d6): δ ppm 7.3-7.04 (m, 5H), 3.78/3.69/3.52/3.21 (dm+m/dm+m, 4H), 3.09 (td, 1H), 2.8 (td, 1H), 2.11/2.11/1.7/1.53 (dm+m/dm+m, 4H), 1.84-1.31 (m, 1H).
$^{13}$C-NMR (125 MHz, MSM-d6): δ ppm 207.5, 173.6, 46.7, 45.1, 43.4/40.3, 41.1/40.7, 33.3/30.5/26.4/25.3.

Step 2: Preparation R1c

1-[trans-2-phenylcyclohexanecarbonyl]piperidin-4-one (1.77 g, 6.2 mmol, 1 eq.) and trimethylsulfoxonium-iodide (3.41 g, 15.5 mmol, 2.5 eq.) was charged into a round bottom flask and dissolved/suspended in MeCN (30 ml). NaOH (0.62 g, 15.5 mmol, 2.5 eq.) was dissolved in water (1.5 ml) and added to the mixture and stirred at 50° C. for 4 hours. After the reaction completed, the solid compound was filtered off and washed with MeCN. The mother liquor was evaporated. The residue was dissolved in DCM and washed with water. The organic layer were dried over MgSO$_4$ and after filtration evaporated to give Preparation R1c. HRMS calculated for $C_{19}H_{25}NO_2$: 299.1885: found 300.1960 [(M+H)$^+$ form].
$^1$H-NMR (500 MHz, MSM-d6) δ ppm 7.28-7.1 (m, 5H), 3.82-2.72 (m, 12H), 2.6-2.5 (m, 2H), 1.85485 (m, 6H).

Preparation R1d: (trans-4,4-difluoro-2-phenyl-cyclohexyl)-1-oxa-6-azaspiro[2.5]octan-6-yl)methanone Step 1: 1-(trans-4,4-difluoro-2-phenyl-cyclohexanecarbonyl)piperidin-4-one 4-Piperidone hydrochloride hydrate (3.14 g, 20.5 mmol). HBTU (11.66 g, 30.74 mmol), trans-4,4-difluoro-2-phenyl-cyclohexanecarboxylic acid (4.92 g, 20.5 mmol) and N,N-diisopropylethylamine (13.26 g 17.8 ml, 102.5 mmol) were dissolved in MeCN (50 mL) and stirred at r.t. for 5 hours. After evaporation, the residue was dissolved in DCM and it was washed with 1N NaOH and then with 1N HCl and then with water. Organic layer was dried (MgSO$_4$) and evaporated. DIPO was added, solid compound was formed, which was filtered off to give the product of the title.

HRMS calculated for $C_{18}H_{21}F_2NO_2$: 321.154: found 322.1633 [(M+H)$^+$ form].

$^1$H-NMR (500 MHz, MSM-d6) δ ppm 7.31-7.14 (m, 5H), 3.86-3.16 (m, 4H), 3.31 (m, 1H), 3.09 (m, 1H), 2.3/2.12 (m+m, 2H), 2.23-1.41 (m, 4H), 2.18-1.97 (m, 2H), 1.88/1.77 (m+m, 2H).

$^{13}$C-NMR (125 MHz, MSM-d6) δ ppm 43.8, 43.1, 39.3, 32.4, 26.7.

Step 2: Preparation R1d 1-(Trans-4,4-difluoro-2-phenyl-cyclohexanecarbonyl)piperidin-4-one (2.0 g, 6.2 mmol, 1 eq.) and trimethylsulfoxonium-iodide (3.4 g, 15.5 mmol, 2.5 eq.) was charged into a round bottom flask and dissolved/suspended in MeCN (11 ml) and MTBE (10 ml). NaOH (0.62 g. 15.5 mmol, 2.5 eq.) was dissolved in water (1.3 ml) and the obtained solution was added to the mixture and stirred at 60° C. for 6 hours. After the reaction completed, the reaction mixture was filtered through Celite. and washed with MTBE (3×4 ml). Water (15 ml) was added to the solution, layers were separated, and the aqueous layer was extracted with MTBE (2×4 ml). Combined organic layers were dried over MgSO$_4$ and after filtration evaporated to give Preparation R1d. HRMS calculated for $C_{19}H_{23}F_2NO_2$: 335.1697: found 336.1779 [(M+H)$^+$ form].

$^1$H-NMR (500 MHz, MSM-d6) δ ppm 7.4-7 (m, 5H), 3.85-2.9 (m, 4H), 3.28 (m, 1H), 3.07 (brm, 1H), 2.59-2.5 (m, 2H), 2.36-2.05 (m, 2H), 2.17-1.96 (m, 2H), 1.83/1.74 (dm+tm, 2H), 1.38-0.79 (m, 4H).

$^{13}$C-NMR (125 MHz, MSM-d6) δ ppm 57.4/57, 53.4/53, 43.7, 42.8, 39.4, 32.4, 26.7.

Preparation R2b: 7-[4-(hydroxymethyl)phenyl]-3H-pyrrolo[2,3-d]pyrimidin-4-one

Using General Procedure 1 starting from Preparation R1b and 4-iodobenzyl alcohol as reagents. Preparation R2b was obtained. HRMS calculated for $C_{13}H_{11}N_3O_2$: 241.0851; found 242.0925 [(M+H)$^+$ form].

$^1$H-NMR (500 MHz, MSM-d6): δ (ppm) 12.07 (brs, 1H), 7.94 (s, 1H), 7.66 (m, 2H), 7.47 20 (m, 2H), 7.45 (d, 1H), 6.67 (d, 1H), 5.31 (t, 1H), 4.56 (d, 2H).

$^{13}$C-NMR (125 MHz, MSM-d6): δ (ppm) 158.9, 147.4, 144.6, 142.2, 136.6, 127.6, 124.3, 124.2, 109.9, 103.5, 62.8.

Preparation R2c: 7-(4-chlorophenyl)-3H-pyrrolo[2,3-d]pyrimidin-4-one

Using General Procedure 1 starting from Preparation R1b and 1-chloro-4-iodobenzene as reagents. Preparation R2c was obtained. HRMS calculated for $C_{12}H_8ClN_3O$: 245.0356; found 246.0427 [(M+H)$^+$ form].

$^1$H-NMR (5 MHz, MSM-d6): δ (ppm) 12.15 (brs, 1H), 7.97 (d, 1H), 7.78 (dm, 1H), 7.61 (dm, 1H), 7.53 (d, 1H), 6.7 (d, 1H).

Preparation R2d: 7-(4-methoxyphenyl)-3H-pyrrolo[2,3-d]pyrimidin-4-one

Using General Procedure 1 starting from Preparation R1b and 4-iodoanisole as reagents. Preparation R2d was obtained. HRMS calculated for $C_{13}H_{11}N_3O_2$: 241.0851: found 242.0929 [(M+H)$^+$ form].

$^1$H-NMR (500 MHz, MSM-d6): δ (ppm) 12.04 (brs, 1H), 7.92 (d, 1H), 7.58 (dd, 1H), 7.4 (d, 1H), 7.08 (d, 1H) 6.65 (d, 1H), 3.81 (s, 3H).

$^{13}$C-NMR (125 MHz, MSM-d6): δ (ppm) 158.8, 158.8, 147.3, 144.4, 130.9, 126.1, 124.4, 114.8, 109.4, 103.1, 55.9.

Preparation R2e: 7-phenyl-3-pyrrolo[2,3-d]pyrimidin-4-one

Using General Procedure 1 starting from Preparation R1b and iodobenzene as reagents, Preparation R2e was obtained. HRMS calculated for $C_{12}H_9N_3O$: 211.0746: found 212.083 [(M+H)$^+$ form].

$^1$H-NMR (500 MHz, MSM-d6): δ(ppm) 12.1 (brs, 1H), 7.95 (d, 1H), 7.71 (m, 2H), 7.54 (m, 2H), 7.5 (d, 1H), 7.4 (m, 1H), 6.69 (d, 1H).

$^{13}$C-NMR (125 MHz, MSM-d6): δ (ppm) 158.8, 147.3, 144.6, 137.8, 129.7, 127.4, 124.6, 124.1, 109.9, 103.6.

Preparation R2f 7-(3-thienyl)-3H-pyrrolo[2,3-d]pyrimidin-4-one

Using General Procedure 7 starting from Preparation Rim and thiophene-3-boronic acid pinacol ester as reagents. Preparation R2f was obtained. HRMS calculated for $C_{10}H_7N_3OS$: 217.0310: found 218.03901 [(M+H)$^+$ form].

$^1$H-NMR (500 MHz, MSM-d6): δ (ppm) 12.14 (s, 1H), 7.99 (d, 1H), 7.92 (dd, 1H), 7.71 (dd, 1H), 7.68 (dd, 1H), 7.57 (d, 1H), 6.66 (d, 1H).

$^{13}$C-NMR (125 MHz, MSM-d6): δ(ppm) 158.6.147, 144.8, 136.3.127, 123.8, 123.3, 115.1, 109.5, 103.5.

Preparation R2o: 7-isopropyl-3H-pyrrolo[2,3-d]pyrimidin-4-one

Using General Procedure 2 starting from Preparation R1a and 2-iodopropane as reagents. Preparation R2o was obtained. HRMS calculated for $C_9H_{11}N_3O$: 177.0902: found 178.0979 [(M+H)+ form].

$^1$H-NMR (500 MHz, MSM-d6): δ (ppm) 11.83 (brs, 1H), 7.87 (s, 1H), 7.24 (d, 1H), 6.47 (d, 1H), 4.85 (sept., 1H), 1.42 (d, 6H).

$^{13}$C-NMR (125 MHz, MSM-d6): δ (ppm) 158.8, 146.8, 143.5, 120.7, 108.2, 102, 46.5, 23.

Preparation R2D: 7-cyclopropyl-3H-pyrrolo[2,3-d]pyrimidin-4-one

Using General Procedure 7 starting from Preparation R1a and cyclopropylboronic acid as reagents. Preparation R2p was obtained. HRMS calculated for $C_9H_9N_3O$: 175.0746; found 176.0919 [(M+H)+ form].

$^1$H-NMR (500 MHz, MSM-d6): δ (ppm) 11.88 (brs, 1H), 7.89 (brs, 1H), 7.05 (d, 1H), 6.4 (d, 1H), 3.53 (m, 1H), 1.06-0.92 (m, 4H).

Preparation R3a: 3-[(4-hydroxy-4-piperidyl)methyl]-6-[(4-methoxyphenyl)methylamino]pyrido[3,2-d]pyrimidin-4-one hydrochloride 6-Chloro-3H-pyrido[3,2-d]pyrimidin-4-one (1.242 g, 6.67 mmol), tert-butyl 1-oxa-6-azaspiro[2.5]octane-6-carboxylate (2.34 g, 11 mmol) and $K_2CO_3$ (2.76 g, 19.9 mmol) were stirred in DMF (20 ml) at 70° C. for 48 hours. The reaction mixture was filtered, and the resulted nitrate was purified by preparative LC (on C-18 Gemini-NX 5 μm column, 5 mM aqueous $NH_4HCO_3$-MeCN, gradient), to give tert-buty 4-[(6-chloro-4-oxo-quinazolin-3-yl)methyl]-4-hydroxy-piperidine-1-carboxylate.

A part of the compound obtained above (3×mg, 0.76 mmol) was dissolved in p-methoxybenzyl amine (3 ml) and heated and stirred at 110° C. for 2 hours. The reaction mixture was purified by preparative LC (on C-18 Gemini-NX 5 µm column, 5 mM aqueous $NH_4HCO_3$-MeCN, gradient), to give tert-butyl 4-hydroxy-4-[[6-[(4-methoxyphenyl)methylamino]-4-oxo-quinazolin-3-yl]methyl]piperidine-1-carboxylate, which was dissolved in aq, 1N HCl solution (4 ml, 4 mmol) and PDO (8 ml) for 3 hours at 70° C. The solvent was evaporated in vacuum to give Preparation R3a. HRMS calculated for $C_{21}H_{25}N_5O_3$: 395.1957: found 396.2044 [(M+H)$^+$ form].

$^1$H-NMR (400 MHz, MSM-d6): δ (ppm) 8.94/8.66 (brd/brq, 2H), 8.28 (s, 1H), 7.92 (brs, 1H), 7.33 (m, 2H), 7.27 (brs, 1H), 6.91 (m, 2H), 4.60 (s, 2H), 4.1 (s, 2H), 3.73 (s, 3H), 3.14 (m, 2H), 2.99 (m, 2H), 1.80 (m, 2H), 1.60 (m, 2H).

$^{13}$C-NMR (100 MHz, MSM-d6): δ (ppm) 146.8, 129.4, 118.5, 114.3, 55.6, 54.1, 44.6, 39.6, 31.5.

Preparation R3b: 3-[(4-hydroxy-4-piperidyl)methyl]-7-(4-methoxyphenyl)pyrrolo[2,3-d]pyrimidin-4-one hydrochloride Using Steps 1 and 2 of General Procedure 3 and starting from Preparation R2d as reagent. Preparation R3b was obtained. HRMS calculated for $C_{19}H_{22}N_3O_3$: 354.1692: found 355.1781 [(M+H)$^+$ form].

$^1$H-NMR (500 MHz, MSM-d6) δ ppm 8.85/8.5 (brd+brq, 2H), 8.16 (s, 1H), 7.59 (m, 2H), 7.44 (d, 1H), 7.09 (m, 2H), 6.68 (d, 1H), 5.25 (s, 1H), 4.07 (s, 2H), 3.82 (s, 3H), 3.14/2.99 (m+m, 4H), 1.78/1.56 (m+m, 4H).

$^{13}$C-NMR (125 MHz, MSM-d6) δ ppm 148.2, 126, 124.8, 114.9, 103.4, 55.9, 53.2, 39.7, 31.5.

Preparation R3c: 3-[(4-hydroxy-4-piperidyl)methyl]-7H-pyrrolo[2,3-d]pyrimidin-4-one hydrochloride Using Steps 1 and 2 of General Procedure 3 and starting from 3,7-dihydropyrrolo[2,3-d] pyrimidin-4-one as reagent. Preparation R3c was obtained. HRMS calculated for $C_{12}H_{16}N_4O_2$: 241.1273: found 249.1342 [(M+H)$^+$ form].

1H-NMR (500 MHz, MSM-d6): δ (ppm) 11.94 (S, 1H), 9.05/8.66 (brd/brq, 2H), 8.10 (s, 1H), 7.05 (dd, 1H), 6.45 (dd, 1H), 4.04 (s, 2H), 3.11 (m, 2H), 2.97 (m, 2H), 1.77 (m, 2H), 1.54 (m, 2H).

$^{13}$C-NMR (125 MHz, MSM-d6): δ (ppm) 158.6, 147.8, 147.5, 121.3, 107.1, 102.7, 53.0, 39.6, 31.5.

Preparation R3d: 3-[(4-hydroxy-4-piperidyl)methyl]-7-methyl-pyrrolo[2,3-d]pyrimidin-4-one hydrochloride Using Steps 1 and 2 of General Procedure 3 and starting from 7-methyl-3H-pyrrolo [2,3-d]pyrimidin-4-one as reagent. Preparation R3d was obtained. HRMS calculated for $C_{13}H_{18}N_4O_2$: 262.143: found 263.114 [(M+H)$^+$ form].

$^1$H-NMR (500 MHz, MSM-d6): δ(ppm) 9.06/8.67 (dm/qm, 2H), 8.16 (s, 1H), 7.12 (d, 1H), 6.47 (d, 1H), 4.05 (s, 2H), 3.71 (s, 3H), 3.10 (m, 2H), 2.96 (m, 2H), 1.76 (m, 2H), 1.53 (m, 2H).

$^{13}$C-NMR (125 MHz, MSM-d6): δ (ppm) 147.6, 125.5, 102.0, 53.5, 39.6, 31.7, 31.5.

Preparation R3e: 3-[(4-hydroxy-4-piperidyl)methyl]-7-phenyl-pyrrolo[2,3-d]pyrimidin-4-one hydrochloride Using Steps 1 and 2 of General Procedure 3 and starting from Preparation R2c as reagent. Preparation R3e was obtained. HRMS calculated for $C_{18}H_{20}N_4O_2$: 324.1586: found 325.1667 [(M+H)$^+$ form].

$^1$H-NMR (500 MHz, MSM-d6) δ: ppm 8.9/8.54 (brq+brd, 2H), 8.19 (s, 1H), 7.72 (m, 2H), 7.56 (m, 2H), 7.53 (d, 1H), 7.42 (m, 1H), 6.72 (d, 1H), 5.3 (s, 1H), 4.08 (s, 2H), 3.15/2.99 (m+m, 4H), 2.57/1.79 (m+m, 4H).

$^{13}$C-NMR (125 MHz, MSM-d6) δ: ppm 158.5, 148.3, 146.6, 137.7, 129.9, 127.5, 124.6, 124.5, 108.8, 103.9, 67.9, 53.2, 39.6, 31.5.

Preparation R3f: 3-[(4-hydroxy-4-piperidyl)methyl]pyrido[3,2-d]pyrimidin-4-one hydrochloride Using Steps 1 and 2 of General Procedure 3 and starting from 3H-pyrido[3,2-d]pyrimidin-4-one as reagent. Preparation R3f was obtained. HRMS calculated for $C_{13}H_{16}N_4O_2$: 260.1273: found 261.1347 [(M+H)$^+$ form].

$^1$H-NMR (500 MHz, MSM-d6) δ: ppm 9.1/8.81 (d/q, 2H), 0.82 (dd, 1H), 8.43 (s, 1H), 8.14 (dd, 1H), 7.85 (dd, 1H), 4.11 (s, 2H), 3.12 (bm, 2H), 2.98 (bm, 2H), 1.82 (bm, 2), 1.61 (bm, 2H).

$^{13}$C-NMR (25 MHz, MSM-d6) δ: ppm 160.0, 150.3, 149.8, 145.1, 138.4, 136.1, 129.4, 61.1, 54.0, 39.5, 31.5.

Preparation R3: 7-[4-(hydroxymethyl)phenyl]-3-[(4-hydroxy-4-piperidyl)methyl]pyrrolo[2,3-d]pyrimidin-4-one hydrochloride Using Steps 1 and 2 of General Procedure 3 and starting from Preparation R2b as reagent. Preparation R3g was obtained. HRMS calculated for $C_{19}H_{22}N_4O_3$: 354.1692: found 355.1769 [(M+H)$^+$ form].

$^1$H-NMR (400 MHz, MSM-d6) δ: ppm 8.76 (brs, 2H), 8.19 (s, 1H), 7.66 (m, 2H), 7.5 (d, 1H), 7.48 (m, 2H), 6.7 (d, 1H), 5.33 (t, 1H), 5.31 (s, 1H), 4.56 (d, 2H), 4.08 (s, 2H), 3.13/2.99 (m+m, 4H), 1.79/1.57 (m+m, 4H).

$^{13}$C-NMR (100 MHz, MSM-d6) δ: ppm 148.3, 127.6, 124.6, 124.2, 103.6, 62.7, 53.1, 39.6, 31.4.

Preparation R3: 7-chloro-3-[(4-hydroxy-4-piperidyl)methyl]thieno[3,4-d]pyrimidin-4-one hydrochloride Using Steps 1 and 2 of General Procedure 3 and starting from 7-chloro-3H-thieno[3,4-d] pyrimidin-4-one as reagent. Preparation R3h was obtained. HRMS calculated for $C_{12}H_{14}ClN_3O_2$: 299.0495: found 300.0573 [(M+H)$^+$ form].

$^1$H-NMR (500 MHz, MSM-d6) δ: ppm 9.11/8.8 (d, mH), 8.43 (s, 1H), 8.11 (s, 1H), 5.14 (brs, 1H), 3.96 (s, 2), 3.1/2.96 (4H), 1.77/1.57 (m 4H).

$^{13}$C-NMR (125 MHz, MSM-d6) δ: ppm 149.3, 126.1, 53.1, 39.5, 31.4.

Preparation 0.4: (1S,2S,3R or 1R,2R,3S)-3-hydroxy-2-phenyl-cyclohexanecarboxylic acid, enantiomer 1 and Preparation R4e: (1S,2S,3S or 1R,2R,3R)-3-hydroxy-2-phenyl-cyclohexanecarboxylic acid, enantiomer 1 and Preparation R4f: (1S,2S,3R or 1R,2R,3S)-3-hydroxy-2-phenyl-cyclohexanecarboxylic acid, enantiomer 2 and Preparation R4g: (1S,2S,3S or 1R,2R,3R)-3-hydroxy-2-phenyl-cyclohexanecarboxylic acid, enantiomer 2

To a 250 mL round-bottom flask, were sequentially added Pd(OAc)$_2$ (0.25 mmol), 2-(di-tert-butylphosphino)biphenyl (0.55 mmol), 1,3-cyclohexanedione (25.2 mmol), and powdered K$_3$PO$_4$ (50.5 mmol). The resulting mixture was degassed (three times) by vacuum/N$_2$ backfills. The vessel was then charged with PDO (100 mL) and chlorobenzene (32.8 mmol). The vessel degassed (three times) with vacuum/N$_2$ backfills. The resulting slurry was heated to reflux for 16 h and cooled to r.t., and water (75 mL) was added. To the homogeneous solution was added concentrated HCl to adjust the pH to 1 and the slurry was stirred for 2.5 h. The slurry was then filtered and the mother liquor was extracted with EEO (3×200 ml). The combined organic layer was dried (MgSO$_4$) and evaporated. It was purified by flash chromatography (DCM:MeOH) to give 3-hydroxy-2-phenyl-cyclohex-2-en-1-one. 3-hydroxy-2-phenyl-cyclohex-2-en-1-one was dissolved in 1,2-dichloroethane and phosphorous tribromide (1.5 eq.) was added. It was heated and stirred at 90° C. for 40 minutes and cooled to 20° C. and poured over cracked ice. Saturated aqueous NaHCO$_3$ solution was added till pH=7 and the solution was extracted with DCM. The organic layer was dried over MgSO$_4$ and the solvent was removed under reduced pressure to give 3-bromo-2-phenyl-cyclohex-2-en-1-one.

A solution of the 3-bromo-2-phenyl-cyclohex-2-en-1-one (I eq.), Pd(PPh$_3$)$_2$Cl$_2$ (0.03 eq.), and n-tributylamine (2 eq.) in EtOH (c=0.3M) was heated at 70° C. under K bar CO in autoclave for 20 hours. The mixture was cooled to r.t. and purified by preparative HPLC (on C-18 Gemini-NX 5 µm column, 5 mM aqueous NH$_4$HCO$_3$-MeCN, gradient) to give the unsaturated carboxylic ester.

The unsaturated carboxylic ester was dissolved in EtOH and palladium on carbon (10%, 0.01 eq.) and ammonium formate (2K eq.) were added. The reaction mixture was heated and stirred at 70° C. for 3 hours, then it was purified by preparative HPLC (on C-18 Gemini-NX 5 µm column, 5 mM aqueous NH$_4$HCO$_3$-MeCN, gradient) to give trans ethyl 3-oxo-2-phenyl-cyclohexanecarboxylate. Enantiomers were separated by chiral chromatography to give ethyl trans-3-oxo-2-phenyl-cyclohexanecarboxylate enantiomer 1 and ethyl trans-3-oxo-2-phenyl-cyclohexanecarboxylate enantiomer 2.

Ethyl trans-3-oxo-2-phenyl-cyclohexanecarboxylate enantiomer 1 was dissolved in EtOH and cooled to 0° C. and then sodium borohydride (1 eq.) was added and it was allowed to warm to r.t. After 30 minutes, water was added then the diastereomers were separated by preparative HPLC (on C-18 Gemini-NX 5 m column, 5 mM aqueous NH$_4$HCO$_3$-MeCN. ISO46) to give ethyl (1S,2S,3R or 1R,2R,3S)-3-hydroxy-2-phenyl-cyclohexanecarboxylate enantiomer 1 and ethyl (1S,2S,3S or 1R,2R,3R)-3-hydroxy-2-phenyl-cyclohexanecarboxylate enantiomer 1.

Ethyl (1S,2S,3R or 1R,2R,3S)-3-hydroxy-2-phenyl-cyclohexanecarboxylate enantiomer 1 was dissolved in the mixture of EtOH and water (1:1 v/v) and lithium hydroxide monohydrate (4 eq.) was added. It was reacted in Anton Paar microwave system for 6 hours at 80° C. Then EtOH was evaporated and 1N HCl solution was added. Solid compound was formed, which was filtered of to give Preparation R4d. HRMS calculated for C$_{13}$H$_{16}$O$_3$: 220.109: found 238.1441 [(M+NH$_4$)$^+$ form].

$^1$H-NMR (54M MHz, MSM-d6) δ: ppm 11.74 (brs, 1H), 7.35-7.05 (m, 5H), 4.31 (d, 1H), 3.49 (m, 1H), 2.52 (m, 1H), 2.5 (m, 1H), 1.93/1.29 (m+m, 2H), 1.84/1.37 (m+m, 2H), 1.7611.46 (m+m, 2H).

$^{13}$C-NMR (125 MHz, MSM-d6) δ: ppm 72.4, 54.1, 49.4, 36.3, 30.2, 24.

Ethyl (1S,2S,3S or 1R,2R,3R)-3-hydroxy-2-phenyl-cyclohexanecarboxylate enantiomer 1 was dissolved in the mixture of EtOH and water (1:1 v/v) and lithium hydroxide monohydrate (4 eq.) was added. It was reacted in Anton Paar microwave system for 6 hours at 80° C. Then EtOH was evaporated and 1N HCl solution was added. Solid compound was formed, which was filtered off, to give Preparation R4e. HRMS calculated for C$_{13}$H$_{16}$O$_4$: 220.1099: found 238.1447 [(M+NH$_4$)$^+$ form].

$^1$H-NMR (500 MHz, MSM-d6) δ: ppm 11.72 (brs, 1H), 7.35-7.05 (m, 5H) 4.43/1.93 (m+m, 2H), 4.33 (d, 1H), 3.77 (m, 1H), 3 (m, 1H), 2.77 (dd, 1H), 1.76/1.49 (m+m, 2H), 1.74/1.59 (m+m, 2H).

$^{13}$C-NMR (125 MHz, MSM-d6) δ: ppm 68.9, 50.2, 42.3, 34, 30.5, 19.2

Ethyl trans-3-oxo-2-phenyl-cyclohexanecarboxylate enantiomer 2 was dissolved in EtOH and cooled to 0° C. and then sodium borohydride (eq.) was added and it was allowed to warm up to r.t. After 30 minutes, water was added, then the diastereomers were separated by preparative HPLC (on C-18 Gemini-NX 5 µm column, 5 mM aqueous NH$_4$HCO$_3$-MeCN. ISO42) to give ethyl (1S,2S,3R or 1R,2R,3S)-3-hydroxy-2-phenyl-cyclohexanecarboxylate enantiomer 2 and ethyl (1S,2S,3S or 1R,2R,3R)-3-hydroxy-2-phenyl-cyclohexanecarboxylate enantiomer 2.

Ethyl (1S,2,3R or 1R,2R,3S)-3-hydroxy-2-phenyl-cyclohexanecarboxylate enantiomer 2 was dissolved in the mixture of EtOH and water 1:1 v/v) and lithium hydroxide monohydrate (4 eq.) was added. It was reacted in Anton Paar microwave system for 6 hours at 8° C. Then EtOH was evaporated and 1N HCl solution was added. Solid compound was formed, which was filtered of, to give Preparation R4f. HRMS calculated for C$_{13}$H$_{16}$O$_5$: 220.1099 found 238.1441 [(M+NH$_4$)$^+$ form].

$^1$H-NMR (500 MHz, MSM-d6) δ: ppm 11.74 (brs, 1H), 7.35-7.05 (m, 5H), 4.31 (d, 1H), 3.49 (m, 1H), 2.52 (m, 1H), 2.5 (m, 1H), 1.93/1.29 (m+m, 2H), 1.84/1.37 (m+m, 2H), 1.76/1.46 (m+m, 2H).

$^{13}$C-NMR (125 MHz, MSM-d6) δ: ppm 72.4, 54.1, 49.4, 36.3, 30.2, 24.

Ethyl (1S,2S,3S or 1R,2R,3R)-3-hydroxy-2-phenyl-cyclohexanecarboxylate enantiomer 2 was dissolved in the mixture of EtOH and water (1:1 v/v) and lithium hydroxide monohydrate (4 eq.) was added. It was reacted in Anton Paar microwave system for 6 hours at 80° C. Then EtOH was evaporated and 1N HCl solution was added. Solid compound was formed, which was filtered off, to give Preparation R4g. HRMS calculated for C$_{13}$H$_{16}$O$_6$: 220.1099: found 238.1439 [(M+NH$_4$)$^+$ form].

$^1$H-NMR (5) M. MSM-d6) δ: ppm 11.72 (brs, 1H), 7.35-7.05 (m, 5H), 4.43/1.93 (m+m, 2H), 4.33 (d, 1H), 3.77 (m, 1H), 3 (m, 1H), 2.77 (dd, 1H), 1.76/1.49 (m+m, 2H), 1.74/1.59 (m+m, 2H).

$^{13}$C-NMR (125 MHz. MSM-d6) δ: ppm 68.9, 50.2, 42.3, 34, 30.5, 19.2

Preparation R4h:
5-fluoro-2-phenyl-cyclohexanecarboxylic acid

A mixture of cinnamic acid, 1,4-hydroquinone (catalytic amount) were suspended in 1,4-butadiene (20 wt % in toluene), and the resulted mixture was heated together in a sealed tube or microwave vial at 200° C. for 2 h. After being cooled to r.t., the sealed tube was cooled in an ice/water bath. Solid compound was formed which was filtered off, and it was washed with cold toluene three times and dried in air, then in vacuo, to afford trans-6-phenylcyclohex-3-ene-1-carboxylic acid.

A part of this was dissolved in chloroform and cooled down to 0° C. Bromotrimethylsilane (eq.) in chloroform and MSM was added dropwise to the cooled solution. Then, diisopropylethylamine (1 eq.) was added dropwise at 0° C. to the mixture. It was stirred for 15 minutes at 0° C. was warmed up to r.t., then it was refluxed overnight. Reaction mixture was diluted with EEO, and washed with water, 10% HCl solution, water and finally with brine. The organic layer was dried ($MgSO_4$) and evaporated. The isolated product was used without further purification.

The isolated product was dissolved in methanol (c=0.2M) and freshly prepared sodium methoxide (1 eq.) was added and stirred at 40° C. for 16 h. The mixture was then treated with 0.5M HCl solution, and the methanol was evaporated. The residue was dissolved in EEO and washed with water and the layers were separated. The aqueous layer was extracted with additional EEO, and the combined organic layers were washed with water, 5% $N_2CO_3$ solution and brine, and dried ($Na_2SO_4$) to give methyl trans-3-oxo-2-phenyl-cyclohexanecarboxylate as a crude product.

Methyl trans-5-oxo-2-phenyl-cyclohexanecarboxylate was dissolved in methanol and sodium borohydride (2 eq.) was added in small portions at 0° C. Reaction mixture was stirred at 0° C. for 1 h, then it was allowed to warm up to r.t. Then water was added, and the reaction mixture was extracted with EEO. Combined organic layers were washed with brine, dried ($MgSO_4$) and evaporated.

The obtained crude material was dissolved in DCM, then DAST was added (S eq.). After 1 h. water and DCM was added, then layers were separated. Organic layer was dried over $MgSO_4$ and the solvent was evaporated. The residue was purified by flash chromatography (hexane:EEO). Then the purified product was dissolved in isopropyl alcohol and cc. HCl (5 eq.) was added. It was heated and stirred at 90° C. for 4 days, then the solid compound was filtered off and it was purified by preparative HPLC (on C-18 Gemini-NX 5 μm column, 0.02% HCOOH aqueous solution-MeCN, gradient) to give Preparation R4h. HRMS calculated for $C_{13}H_{15}FO_2$: 222.1056: found 222.2 (GCMS).

$^1$H-NMR (500 MHz, MSM-d6) δ: ppm 11.97 (brs, 1H), 7.32-7.13 (m, 5H), 5 (dm, 1H), 2.8 (m, 1H), 2.78 (m, 1H), 2.2/1.78 (m+m, 2H), 2/1.73 (m+m, 2H), 1.69/1.6 (m+m, 2H)

$^{13}$C-NMR (125 MHz, MSM-d6) δ: ppm 8.1, 45.1, 44, 34.2, 30.3, 28.5

Preparation R4l: trans-2-(1-ethylpyrazol-4-yl)-4,4-difluoro-cyclohexanecarboxylic acid Using Step 1 of General Procedure 9 and starting from 1-ethyl-1H-pyrazole-4-carbaldehyde. (E)-4-(1-ethyl-1H-pyrazol-4-yl)but-3-en-2-one was obtained. It was dissolved in DCM and DBU (1.3 eq.) was added. Then. TMSCl (1.2 eq.) was added dropwise at 0° C. The solution was stirred for 2 hours at 40° C. then cooled and washed with $NaHCO_3$ solution 3 times. The organic layer was dried over $MgSO_4$, then the solvent was evaporated under reduced pressure. (E)-1-ethyl-4-(3-((trimethylsilyl)oxy)buta-1,3-dien-1-yl)-1H-pyrazole was used without further purification according to Steps 3 to 5 of General Procedure 9 to give Preparation R4l. HRMS calculated for $C_{12}H_{16}F_2N_2O_2$:258.118: found 259.1249 [(M+H)$^+$ form].

$^1$H-NMR (500 MHz, MSM-d6) δ ppm 12.18 (s, 1H), 7.55 (s, 1H), 7.29 (s, 1H), 4.04 (q, 2H), 2.92 (td, 1H), 2.43 (td, 1H), 2.2-1.96 (m, 2H), 2.15-1.84 (m, 2H), 1.99/1.62 (d+qd, 2H), 1.31 (t, 3H)

$^{13}$C (500 MHz, MSM-d6) δ ppm 175.9, 137.2, 127.3, 122.3, 48.9, 46.5, 40, 33.4, 32.3, 26.3, 15.9

Preparation R4s: trans-2-methyl-6-(2-thienyl)cyclohex-2-ene-1-carboxylic acid

Mixture of methyl acetoacetate (1 eq.), thiophene-2-carbaldehyde (2 eq.) and piperidine (1 eq., 50% solution in MeOH) were dissolved in MeOH and water (1:1) and allowed to stand at r.t. for 49 hours, then it was heated and stirred in Anion Paar microwave system for 30 minutes at 85° C. Then it was cooled to r.t. and 6M HCl solution was slowly added, and then it was extracted with DEE. The organic layer was dried over $MgSO_4$ and the solvent was evaporated. The crude product was purified by flash chromatography (hexane:EEO) to give the corresponding unsaturated ketone derivative.

The corresponding unsaturated ketone derivative was dissolved in DCM and triethylsilane (6eq.) and boron trifluoride diethyl etherate (6 eq.) were added. It was stirred at r.t. for 24 hours, then it was evaporated and purified by flash chromatography (hexane:EEO) to give the corresponding unsaturated ester derivative.

The corresponding unsaturated ester derivative was dissolved in MeOH and water (5:1) and lithium hydroxide hydrate (5 eq.) was added. It was stirred at 50° C. for 95 hours, and then MeOH was evaporated. A 1N HCl solution was added and solid compound was formed, which was filtered off to give Preparation R4s. HRMS calculated for $C_{12}H_{14}O_2S$: 222.0715: found 222.2 (GCMS).

$^1$H-NMR (500 MHz, MSM-d6) δ ppm 12.35 (brs, 1H), 7.33 (d, 1H), 6.93 (dd, 1H), 6.88 (d, H), 5.58 (brs, 1H), 3.38 (td, 1H), 3.06 (d, 1H), 2.13/2.03 (brm+brd, 2H), 1.91/1.66 (m+brm, 2H), 1.66 (brs, 3H).

$^{13}$C-NMR (125 MHz, MSM-d6) δ ppm 174.9, 148.3, 130.2, 127.1, 124.4, 124.1, 124, 54.6, 38.6, 29.7, 24.7, 22.1.

Preparation R4t: trans-2-methyl-6-(3-thienyl)cyclohex-2-ene-1-carboxylic acid

Mixture of methyl acetoacetate (1 eq.), thiophene-3-carbaldehyde (2 eq.) and piperidine (I eq., 50% solution in MeOH) were dissolved in MeOH and water (1:1) and allowed to stand at r.t. for 48 hours, then it was heated and stirred in Anton Paar microwave system for 30 minutes at 85° C. Then it was cooled to r.t. and 6M HCl solution was slowly added, and then it was extracted with DEE. The organic layer was dried over $MgSO_4$ and the solvent was evaporated. The crude product was purified by flash chromatography (hexane:EEO) to give the corresponding unsaturated ketone derivative.

The corresponding unsaturated ketone derivative was dissolved in DCM and triethylsilane (6 eq.) and boron trifluoride diethyl etherate (6 eq.) were added. It was stirred at r.t. for 24 hours, then the solvent was evaporated and the crude product was purified by flash chromatography (hexane:EEO) to give the corresponding unsaturated ester derivative.

The corresponding unsaturated ester derivative was dissolved in MeOH and water (5:1) and lithium hydroxide hydrate (5 eq.) was added. It was stirred at 50° C. for 95 hours, and then MeOH was evaporated. A 1N HCl solution was added, and then it was evaporated. The crude product was purified by preparative HPLC (on C-18 Gemini-NX 5 μm column, 0.02% HCOOH aqueous solution-MeCN, gradient) to give Preparation R4t. HRMS calculated for $C_{12}H_{14}O_2S$: 222.0715: found 222.1 (GCMS).

¹H-NMR (500 MHz, MSM-d6) δ ppm 12.21 (brs 1H), 7.44 (dd, 1H), 7.17/7.04 (dm+dd, 2H), 5.56 (brm, 1H), 3.17 (ddd, 1H) 3.09 (d, 1H), 2.1/1.97 (m+dm, 2H), 1.8/1.63 (dm+m, 2H), 1.66 (brs, 3H).
¹³C-NMR (125 MHz, MSM-d6) δ ppm 175.4, 145.9, 130.6, 127.7/120.6, 126.2, 124.2, 53.4, 38.9, 28.6, 24.8, 22.1.

Preparation R4x:
trans-3,3-difluoro-2-phenyl-cyclohexanecarboxylic add, enantiomer 1

Ethyl trans-3-oxo-2-phenyl-cyclohexanecarboxylate enantiomer 1 (intermediate obtained for Preparations R4d-g) was dissolved in DCM and DAST (5 eq.) was added. The solution was stirred at r.t. for 20 hours, then water was added. Layers were separated and the water layer was washed with DCM. Combined organic layers were dried (MgSO$_4$) and the solvent was evaporated. Then, the residue was purified by preparative HPLC (on C-18 Gemini-NX 5 μm column, 5 mM aqueous NH$_4$HCO$_3$-MeCN gradient).
The obtained compound was dissolved in the mixture of EtOH and water (1:1) and lithium hydroxide monohydrate (4 eq.) was added. It was reacted in Anton Paar microwave system for 6 hours at 80° C. Then EtOH was evaporated and 1 N aq. HCl solution was added. Solid compound was formed, which was filtered off, to give Preparation R4x. HRMS calculated for $C_{13}H_{14}F_2O_2$: 240.092: found 239.0875 [(M+H)$^+$ form].
¹H-NMR (50 MHz, MSM-d6) δ ppm 12.23 (brs, 1H), 7.4-7.12 (m, 5H), 3.25 (ddd, 1H), 2.94 (td, 1H), 2.11/1.97 (m+m, 2H), 2.01/1.58 (m+m, 2H), 1.88/1.63 (m+m, 2H).
¹³C-NMR (125 MHz, MSM-d6) δ ppm 174.6, 124, 51.2, 46.5, 34.1, 29, 22.2.

Preparation R4v:
trans-3,3-difluoro-2-phenyl-cyclohexanecarboxylic add, enantiomer 2

Ethyl trans-3-oxo-2-phenyl-cyclohexanecarboxylate enantiomer 2 (intermediate obtained for Preparations R4d-g) was dissolved in DCM and DAST (5 eq.) was added. The solution was stirred at r.t. for 20 hours, then water was added. Layers were separated and the water layer was washed with DCM. Combined organic layers were dried (MgSO$_4$) and evaporated. Then, the residue was purified by preparative HPLC (on C-18 Gemini-NX 5 μm column, 5 mM aqueous NH$_4$HCO$_3$-MeCN gradient).
The obtained compound was dissolved in the mixture of EtOH and water (1:1) and lithium hydroxide monohydrate (4 eq.) was added. It was reacted in Anton Paar microwave system for 6 hours at 80° C. Then EtOH was evaporated and 1N HCl solution was added. Solid compound was formed, which was filtered off to give Preparation R4y. HRMS calculated for $C_{13}H_{14}F_2O_2$: 240.0962: found 239.0890 [(M+H)$^+$ form].
¹H-NMR (500 MHz, MSM-d6) δ ppm 12.23 (brs, 1H), 7.4-7.12 (m, 5H), 3.25 (ddd, 1H), 2.94 (td, 1H), 2.11/1.97 (m+m, 2H), 2.01/1.3 (m+m, 2H), 1.8811.63 (m+m, 2H).
¹³C-NMR (125 MHz, MSM-d6) δ ppm 174.6, 124, 51.2, 46.5, 34.1, 29, 22.2.

Preparation R4z: trans-4,4-difluoro-2-(2-furyl)cyclohexanecarboxylic acid

Using General Procedure 9 and starting from furan-2-carbaldehyde. Preparation R4z was obtained. HRMS calculated for: $C_{11}H_{12}F_2O_3$: 230.0755: found 231.0832 [(M+H)$^+$ form].

¹H-NMR (500 MHz, MSM-d6) δ ppm 12.34 (s, 1H), 7.53 (dd, 1H), 7.36 (dd, 1H), 6.16 (brd, 1H), 3.11 (td, 1H), 2.6 (td, 1H), 2.24/2.06 (m+m, 2H), 2.1-1.9 (m, 2H), 2.03/1.65 (m+m, 2H).
¹³C (500 MHz, MSM-d6) δ ppm 142.3, 123.7, 110.8, 105.8, 46, 37.7, 36.6, 32.1, 26.2.

Preparation R4aa: trans-4,4-difluoro-2-(3-furyl)cyclohexanecarboxylic acid

Using General Procedure 9 and starting from furan-3-carbaldehyde. Preparation R4aa was obtained. HRMS calculated for $C_{11}H_{12}F_2O_3$: 230.0755: found 231.0816 [(M+H)$^+$ form].
¹H-NMR (500 MHz, MSM-d6) δ ppm 12.26 (brs, 1H), 7.55 (m, 1H), 7.47 (m, 1H), 6.48 (m, 1H), 2.92 (m, 1H), 2.48 (m, 1H), 2.17-1.94 (m, 2H), 2.09/1.95 (m+m, 2H), 2/1.63 (m+m, 2H).
¹³C (500 MHz, MSM-d6) δ ppm 143.6, 139.5, 110.2, 47.9, 39.4, 33.7, 32.3, 26.4.

Preparation R4ab: trans-4,4-difluoro-2-(3-thienyl)cyclohexanecarboxylic acid

Using General Procedure 9 and starting from 3-thiophenecarboxaldehyde. Preparation R4ab was obtained. HRMS calculated for $C_{11}H_{12}F_2O_2S$: 246.0526: found 264.0865 [(M+NH$_4$)$^+$ form].
¹H-NMR (500 MHz, MSM-d6) δ ppm 12.15 (brs, 1H), 7.45 (dd, 1H), 7.27 (dd, 1H), 7.09 (dd, 1H), 3.12 (td, 1H), 2.62 (td, 1H), 2.2-2.06 (m, 2H), 2.16-1.88 (m, 2H), 2.02/1.65 (d+q, 2H).
¹³C (500 MHz, MSM-d6) δ ppm 175.6, 127.6, 126.4, 121.7, 48, 39.9, 38.5, 32.3, 26.3.

Preparation R4ac: trans-4,4-difluoro-2-(4-pyridyl) cyclohexanecarboxylic aid

Using General Procedure 9 and starting from isonicotinaldehyde. Preparation R4ac was obtained. HRMS calculated for $C_{12}H_{13}F_2NO_2$: 241.0914: found 242.0994 [(M+H)$^+$ form]. ¹H-NMR (500 MHz, MSM-d6) δ ppm 8.44 (m, 2H), 7.28 (m, 2H), 2.96 (td, 1H), 2.63 (td, 1H), 2.14-1.82 (m, 2H), 2.11-1.94 (m, 2H), 2.03/1.62 (d+qd, 2H). ¹³C (500 MHz, MSM-d6) δ ppm 175.8, 149.9, 123.6, 47.9, 42.8, 39.5, 32.7, 26.9.

Preparation R4ad: trans-4,4-difluoro-2-(5-methyl-3-thienyl)cyclohexanecarboxylic acid Using General Procedure 9 and starting from 5-methyl-thiophene-3-carbaldehyde, Preparation R4ad was obtained. HRMS calculated for $C_{12}H_{14}F_2O_2S$: 260.0683: found 261.0756 [(M+H)$^+$ form].
¹H-NMR (500 MHz, MSM-d6) δ ppm 12.15 (brs, 1H), 6.97 (s, 1H), 6.76 (s, 1H), 3 (m, 1H), 2.57 (m, 1H), 2.38 (s, 3H), 2.16-1.95 (m, 2H), 2.09/1.95 (m+m, 2H), 2/1.63 (m+m, 2H). ¹³C (500 MHz, MSM-d6) δ ppm 125.9, 119.3, 47.9, 39.9, 38.7, 32.3, 26.5, 15.5.

Preparation R4ae: trans-4,4-difluoro-2-[5-(trifluoromethyl)-3-thienyl]cyclohexanecarboxylic add Using General Procedure 9 and starting from 5-(trifluoromethyl)thiophene-3-carbaldehyde. Preparation R4ae was obtained. HRMS calculated for $C_{12}H_{11}F_2O_2S$: 314.04: found 314.03944 (EI).

¹H-NMR (500 MHz, MSM-d6) δ ppm 12.31 (brs, 1H), 7.74 (t, 1H) 7.72 (d, 1H), 3.13 (m, 1H), 2.67 (td, 1H), 2.27-2.12 (m, 2H), 2.11/2.04-1.37 (m+m, 2H), 2.04/1.64 (dm+qd, 2H)
¹³C (500 MHz, MSM-d6) δ ppm 144.2, 130.5, 127.2, 47.7, 39.4, 38.5, 32.3, 26.4.

Preparation R4af: trans-4,4-difluoro-2-oxazol-4-yl-cyclohexanecarboxylic acid

Using General Procedure 9 and starting from oxazole-4-carbaldehyde, Preparation R4af was obtained. HRMS calculated for $C_{10}H_{11}F_2NO_3$: 231.0707: found 232.0786 [(M+H)⁺ form].
¹H-NMR (500 MHz, MSM-d6) δ ppm 12.36 (brs, 1H), 8.3 (m, 1H), 7.87 (m, 1H), 3.03 (m, 1H), 2.6 (m, 1H), 2.19-1.86 (m, 2H), 2.16/2.06 (m+m, 2H), 2.03/1.64 (m+m, 2H). ¹³C (500 MHz, MSM-d6) δ ppm 152.4, 135.5, 46.1, 38.1, 34.5, 32.3, 26.2.

Preparation R4af: trans-4,4-difluoro-2-oxazol-5-yl-cyclohexanecarboxylic acid

Using General Procedure 9 and starting from oxazole-5-carbaldehyde. Preparation R4af was obtained. HRMS calculated for $C_{12}H_{11}F_2NO_3$: 231.0707: found 232.0790 [(M+H)⁺ form].
¹H-NMR (501 MHz, MSM-d6) δ ppm 12.56 (brs, 1H), 9.28 (s, 1H), 6.94 (s, 1H), 3.18 (m, 1H), 2.64 (m, 1H), 2.25/2.11 (m+m, 2H), 2.15-1.93 (m, 2H), 2.05/1.64 (m+m, 2H).
¹³C (500 MHz, MSM-d6) δ ppm 151.7, 122.4, 45.7, 37.1, 34.5, 32, 26.1.

Preparation R4ah: trans-4,4-difluoro-2-phenyl-cyclohexanecarboxylic acid 2-trimethylsilyloxy-4-phenyl-1,3-butadiene (synthesized according to Tetrahedron 2001, 57, 6311-6327: 1 eq.) and methyl propiolate 1 eq.) were placed in a sealed tube into anhydrous toluene. The reaction mixture was heated to 150° C. and it was stirred at this temperature overnight. Then the toluene was evaporated by reduced pressure and the residue was dissolved in the mixture of THF, water, and cc, sulfuric acid (3 eq.): mixture was stirred for 1 h at 25° C. Reaction mixture was diluted with water (150 ml) and the product was isolated by extraction with DEE. The organic layer was dried and concentrated. Crude product was used without further purification.

The unsaturated cyclohexenone derivative was placed in a flask and dissolved in cyclohexene. The reaction mixture was refluxed overnight in the presence 0.05 eq. 10% Pd/C. After 16 h. the Pd/C was filtered off through Celite pad. The saturated crude product was refluxed in methanol in the presence sodium methoxide to give methyl trans-4-oxo-2-phenyl-cyclohexanecarboxylate.

Methyl trans-4-oxo-2-phenyl-cyclohexanecarboxylate was dissolved in DCM, then DAST was added (5 eq.). After 1 h, water and DCM was added, then layers were separated. Organic layer was dried and evaporated. The residue was purified by flash chromatography (hexane:EEO).

Then the product obtained from the previous step was dissolved in isopropyl alcohol and cc. HCl (5 eq.) was added. It was heated and stirred at 90° C. for 4 days. Then the solid compound was filtered off and it was purified by preparative HPLC (on C-18 Gemini-NX 5 µm column, 0.02% HCOOH aqueous solution-MeCN, gradient) to give Preparation R4ah. HRMS calculated for $C_{13}H_{14}F_2O_2$: 240.0962: found 239.0910 [(M–H) form].
¹H-NMR (500 MHz, MSM-d6) δ ppm 12.06 (s, 1H), 7.34-7.16 (m, 5H), 2.95 (m, 1H), 2.73 (m, 1H), 2.24-2 (m, 2H), 2.2-1.93 (m, 2H), 2.05/1.68 (m+m, 2H).
¹³C-NMR (125 MHz, MSM-d6) δ ppm 124, 47.5, 43.4, 40.2, 32.3, 26.6.

Preparation R4ai: trans-4,4-difluoro-2-thiazol-4-yl-cyclohexanecarboxylic acid

Using General Procedure 9 and starting from thiazole-4-carboxaldehyde. Preparation R4ai was obtained. HRMS calculated for $C_{10}H_{11}F_2NO_2S$: 247.0479: found 248.0562 [(M+H)⁺ form].
¹H-NMR (400 MHz, MSM-d6) δ ppm 12.1K (brs, 1H), 9.03 (d, 1H), 7.42 (d, 1H), 3.2 (m, 1H), 2.75 (m, 1H), 2.28-2.04 (m, 2H), 2.21-1.87 (m 2H), 2.06/1.68 (m+m, 2H).
¹³C (400 MHz. MSM-d6) δ ppm 154.4, 115.2, 46.7, 39.1, 39, 32.4, 26.3

Preparation R4aj: trans-4,4-difluoro-2-(2-thienyl) cyclohexanecarboxylic acid

Using General Procedure 9 and starting from 2-thiophenecarboxaldehyde, Preparation R4ab was obtained as lithium salt. HRMS calculated for $C_{11}H_{12}F_2O_2S$: 246.0526, found 245.0492 [(M–H) form].
¹H-NMR (5W MHz, MSM-d6) δ ppm 7.3-6.9 (m, 3H), 3.3 (m, 1H), 2.16/1.9 (m+m, 2H), 2.13 (m, 1H), 2.01/1.82 (m+m, 2H), 1.9/1.62 (m+m, 2H).
¹³C-NMR (125 MHz, MSM-d6) δ ppm 53, 41.7, 38.7, 33.1, 27.4.

Preparation R4ak: trans-5-difluoro-2-phenyl-cyclohexanecarboxylic acid

A mixture of cinnamic acid, 1,4-hydroquinone (catalytic amount) were suspended in 1,4-butadiene (20 wt % in toluene), and the resulted mixture was heated together in a sealed tube or microwave vial at 200° C. for 2 h. After being cooled to r.t., the sealed tube was cooled in an ice/water both. Solid compound was formed which was filtered off, and it was washed with cold toluene three times and dried in air, then in vacuo, to afford trans-6-phenylcyclohex-3-ene-1-carboxylic acid.

A part of this product was dissolved in chloroform and cooled to 0° C. Bromotrimethylsilane (1 eq.) in chloroform and MSM was added dropwise to the cooled solution. Then, diisopropylethylamine (eq.) was added dropwise at 0° C. to the mixture. It was stirred for 15 minutes at 0° C., was warmed up to r, t., then it was refluxed overnight. Reaction mixture was diluted with EEO, and washed with water, 10% HCl solution, water and finally with brine. The organic layer was dried (MgSO₄) and evaporated. The isolated product was used without further purification.

The isolated product was dissolved in methanol and freshly prepared sodium methoxide (1 eq.) was added and the mixture was stirred at 40° C. for 16 h. The mixture was then treated with 0.5M HCl solution, and methanol was evaporated. The residue was dissolved in EEO and washed with water and the layers were separated. The aqueous layer was extracted with additional EEO, and the combined organic layers were washed with water, 5% Na₂CO₃ and brine, and dried (Na$_2$SO$_4$) to give methyl trans-5-oxo-2-phenyl-cyclohexanecarboxylate as a crude product.

Methyl trans-5-oxo-2-phenyl-cyclohexanecarboxylate was dissolved in DCM, then DAST was added eq.). After 1 h water and DCM was added, then layers were separated. Organic layer was dried and evaporated. The residue was purified by flash chromatography (hexane:EEO).

Then the product obtained from the previous step was dissolved with isopropyl alcohol and cc. HCl (5 eq.) was added. It was heated and stirred at 90° C. for 4 days, then the solid compound was filtered off and it was purified by preparative HPLC (on C-18 Gemini-NX 5 μm column, 0.02% HCOOH aqueous solution—MeCN, gradient) to give Preparation R4ak. HRMS calculated for C$_{13}$H$_{14}$F$_2$O$_2$: 240.0962: found 239.0902 [(M–H) form].

$^1$H-NMR (500 MHz, MSM-d6) δ ppm 12.24 (s, 1H), 7.32-7.16 (m, 5H), 2.87 (m, 1H), 2.77 (m, 1H), 2.32/2.06 (m+m, 2H), 2.16-1.96 (m, 2H), 1.3/1.69 (m+m, 2H).

$^{13}$C-NMR (125 MHz, MSM-d6) δ ppm 123.8, 46.5, 44.6, 36.7, 33.4, 30.7.

EXAMPLES

The following Examples illustrate the invention but do not limit it in any way.

3-[[4-hydroxy-1-[trans-2-(3-thienyl)cyclohexanecarbonyl]-4-piperidyl]methyl]pyrido[3,2-d]pyrimidin-4-one (Example 1)

Using Step 3 of General Procedure 3 and starting from Preparation R3f and 2-(3-thienyl)cyclohexanecarboxylic acid as reagents. EXAMPLE 1 was obtained. HRMS calculated for C$_{24}$H$_{28}$N$_4$O$_3$S: 452.182: found 453.1974 [(M+H)$^+$ form].

3-[[4-hydroxy-1-[trans-2-(3-thienyl)cyclohexanecarbonyl]-4-piperidyl]methyl]-7-methyl-pyrrolo[2,3-d]pyrimidin-4-one (Example 2)

Using Step 3 of General Procedure 3 and starting from Preparation R3d and 2-(3-thienyl)cyclohexanecarboxylic acid as reagents. EXAMPLE 2 was obtained. HRMS calculated for C$_{24}$H$_{30}$N$_4$O$_3$S: 454.2039: found 455.2123 [(M+H)$^+$ form].

3-[[1-[trans-2-(3-furyl)cyclohexanecarbonyl]-4-hydroxy-4-piperidyl]methyl]-7-methyl-pyrrolo[2,3-d]pyrimidin-4-one (Example 3)

Using Step 3 of General Procedure 3 and starting from Preparation R3d and 2-(3-furyl)cyclohexanecarboxylic acid as reagents. EXAMPLE 3 was obtained. HRMS calculated for C$_{24}$H$_{30}$N$_4$O$_4$: 438.2267: found 439.2348 [(M+H)$^+$ form].

3-[[1-[trans-2-(3-furyl)cyclohexanecarbonyl]-4-hydroxy-4-piperidyl]methyl]pyrido[3,2-d]pyrimidin-4-one (Example 4)

Using Step 3 of General Procedure 3 and starting from Preparation R3f and 2-(3-furyl)cyclohexanecarboxylic acid as reagents EXAMPLE 4 was obtained. HRMS calculated for C$_{24}$H$_{28}$N$_4$O$_4$: 436.2111: found 437.2185 [(M+H)$^+$ form].

3-[[4-hydroxy-1-[cis-3-phenyl-1,4-dioxane-2-carbonyl]-4-piperidyl]methyl]-7-phenyl-pyrrolo[2,3-d]pyrimidin-4-one, enantiomer 1 (Example 5)

and

3-[[4-hydroxy-1-[cis-3-phenyl-1,4-dioxane-2-carbonyl]-4-piperidyl]methyl]-7-phenyl-pyrrolo[2,3-d]pyrimidin-4-one, enantiomer 2 (Example 6)

Using Step 3 of General Procedure 3 and starting from Preparation R3e and cis-3-phenyl-1,4-dioxane-2-carboxylic acid as reagents, EXAMPLE 5 and EXAMPLE 6 were obtained separately by chiral chromatography.

EXAMPLE 5: HRMS calculated for C$_{29}$H$_{30}$N$_4$O$_5$: 514.2216: found 515.2289 [(M+H)$^+$ form].

EXAMPLE 6: HRMS calculated for C$_{29}$H$_{30}$N$_4$O$_5$: 514.2216: found 515.2302 [(M+H)$^+$ form].

3-[[4-hydroxy-1-[cis-3-phenyl-1,4-dioxane-2-carbonyl]-4-piperidyl]methyl]-7-(4 methoxyphenyl)pyrrolo[2,3-d]pyrimidin-4-one, enantiomer 1 (Example 7)

and

3-[[4-hydroxy-1-[cis-3-phenyl-1,4-dioxane-2-carbonyl]-4-piperidyl]methyl]-7-(4-methoxyphenyl)pyrrolo[2,3-d]pyrimidin-4-one, enantiomer 2 (Example 8)

Using Step 3 of General Procedure 3 and starting from Preparation R3b and cis-3-phenyl-1,4-dioxane-2-carboxylic acid as reagents. EXAMPLE 7 and EXAMPLE 8 were obtained separately by chiral chromatography.

EXAMPLE 7: HRMS calculated for C$_{30}$H$_{32}$N$_4$O$_6$: 544.2322: found 545.2403 [(M+H)$^+$ form].

EXAMPLE 8: HRMS calculated for C$_{30}$H$_{32}$N$_4$O$_6$: 544.2322: found 545.239 [(M+H)$^+$ form].

3-[[4-hydroxy-1-(trans-2-phenylcyclohexanecarbonyl)-4-piperidyl]methyl]-7-phenyl-pyrrolo[2,3-d]pyrimidin-4-one (Example 9)

Using Step 3 of General Procedure 3 and starting from Preparation R3e and trans-2-phenylcyclohexanecarboxylic acid as reagents. EXAMPLE 9 was obtained. HRMS calculated for C$_{31}$H$_{34}$N$_4$O$_3$: 510.2631: found 511.2718 [(M+H)$^+$ form].

3-[[4-hydroxy-1-(1-phenylpiperidine-2-carbonyl)-4-piperidyl]methyl]-7-(4-methoxyphenyl)pyrrolo[2,3-d]pyrimidin-4-one (Example 10)

Using Step 3 of General Procedure 3 and starting from Preparation R3b and 1-phenylpiperidine-2-carboxylic acid as reagents. EXAMPLE 10 was obtained. HRMS calculated for C$_{31}$H$_{35}$N$_5$O$_4$: 541.2689: found 542.2757 [(M+H)$^+$ form].

3-[[4-hydroxy-1-(1-phenylpyrrolidine-2-carbonyl)-4-piperidyl]methyl]-7-(4-methoxyphenyl)pyrrolo[2,9-d]pyrimidin-4-one (Example 11)

Using Step 3 of General Procedure 3 and starting from Preparation R3b and 1-phenylpyrrolidine-2-carboxylic acid as reagents, EXAMPLE 11 was obtained. HRMS calculated for $C_{30}H_{33}N_5O_4$: 527.2532: found 52.2598 [(M+H)$^+$ form].

3-[[4-hydroxy-1-[trans-2-pyrrol-1-ylcyclohexanecarbonyl]-4-piperidyl]methyl]-7-phenyl-pyrrolo[2,3-d]pyrimidin-4-one, racemic (Example 12)

and

3-[[4-hydroxy-1-[trans-2-pyrrol-1-ylcyclohexanecarbonyl]-4-piperidyl]methyl]-7-phenyl-pyrrolo[2,3-d]pyrimidin-4-one, enantiomer 1 (Example 13)

and

3-[[4-hydroxy-1-[trans-2-pyrrol-1-ylcyclohexanecarbonyl]-4-piperidyl]methyl]-7-phenyl-pyrrolo[2,3-d]pyrimidin-4-one, enantiomer 2 (Example 14)

Using Step 3 of General Procedure 3 and starting from Preparation R3e and 2-pyrrol-1-ylcyclohexanecarboxylic acid as reagents, EXAMPLE 12 was obtained. EXAMPLE 13 and EXAMPLE 14 were obtained separately by chiral chromatography.

EXAMPLE 12: HRMS calculated for $C_{29}H_{33}N_5O_3$: 499.253: found 522.2478 [(M+Na)$^+$ form].
EXAMPLE 13: HRMS calculated for $C_{29}H_{33}N_5O_3$: 499.2583: found 500.2667 [(M+H)$^+$ form].
EXAMPLE 14: HRMS calculated for $C_{29}H_{33}N_5O_3$: 499.2583: found 500.2665 [(M+H)$^+$ form.

3-[[4-hydroxy-1-trans-2-pyrrol-1-ylcyclohexanecarbonyl]-4-piperidyl]methyl]-7-(4-methoxyphenyl)pyrrolo[2,3-d]pyrimidin-4-one, racemic (Example 15)

and

3-[[4-hydroxy-1-[trans-2-pyrrol-1-ylcyclohexanecarbonyl]-4-piperidyl]methyl]-7-(4-methoxyphenyl)pyrrolo[2,3-d]pyrimidin-4-one, enantiomer 1 (Example 16)

and

3-[[4-hydroxy-1-[trans-2-pyrrol-1-ylcyclohexanecarbonyl]-4-piperidyl]methyl]-7-(4-methoxyphenyl)pyrrolo[2,3-d]pyrimidin-4-one, enantiomer 2 (Example 17)

Using Step 3 or General Procedure 3 and starting from Preparation R3b and 2-pyrrol-1-ylcyclohexanecarboxylic acid as reagents, EXAMPLE 15 was obtained. EXAMPLE 16 and EXAMPLE 17 were obtained separately by chiral chromatography.

EXAMPLE 15: HRMS calculated for $C_{30}H_{35}N_5O_4$: 529.26H$_9$: found 530.2759 [(M+H)$^+$ form].
EXAMPLE 16: HRMS calculated for $C_{30}H_{35}N_5O_4$: 529.2689: found 530.2766 [(M+H)$^+$ form].
EXAMPLE 17: HRMS calculated for $C_{30}H_{35}N_5O_4$: 529.2689: found 530.277 [(M+H)$^+$ form].

6-[[4-hydroxy-1-(trans-2-phenylcyclohexanecarbonyl)-4-piperidyl]methyl]-3-phenyl-triazolo[4,5-d]pyrimidin-7-one (Example 18)

Using General Procedure 4 starting from 3-phenyl-6H-triazolo[4,5-d]pyrimidin-7-one and Preparation R1c as reagents. EXAMPLE 18 was obtained. HRMS calculated for $C_{29}H_{32}N_6O_3$: 512.2536: found 513.2606 [(M+H)$^+$ form].

5-[[4-hydroxy-1-(trans-2-phenylcyclohexanecarbonyl)-4-piperidyl]methyl]-1-phenyl-pyrazolo[3,4-d]pyrimidin-4-one (Example 19)

Using General Procedure 4 starting from 1-phenyl-H-pyrazolo[3,4-d]pyrimidin-4-one and Preparation R1c as reagents. EXAMPLE 19 was obtained. HRMS calculated for $C_{30}H_{33}N_5O_3$: 512.253: found 512.2652 [(M+H)$^+$ form].

1-[[4-hydroxy-1-(trans-2-phenylcyclohexanecarbonyl)-4-piperidyl]methyl]-9-phenyl-purin-6-one (Example 20)

Using General Procedure 4 starting from 9-phenyl-1H-purin-6-one and Preparation R1c as reagents. EXAMPLE 20 was obtained. HRMS calculated for $C_{30}H_{33}N_5O_3$: 511.2583: found 512.2651 [(M+H)$^+$ form].

3-[[4-hydroxy-1-(trans-2-phenylcyclohexanecarbonyl) 4-piperidyl]methyl]-7-(4-methoxyphenyl)pyrrolo[2,3-d]pyrimidin-4-one (Example 21)

Using General Procedure 4 starting from Preparation R2d and Preparation R1c as reagents. EXAMPLE 21 was obtained. HRMS calculated for $C_{32}H_{36}N_4O_4$: 540.2737: found 541.2806 [(M+H)$^+$ form].

7-(4-chlorophenyl)-3-[[4-hydroxy-1-(trans-2-phenylcyclohexanecarbonyl)-4-piperidyl]methyl]pyrrolo[2,3-d]pyrimidin-4-one (Example 22)

Using General Procedure 4 starting from Preparation R2c and Preparation R1c as reagents. EXAMPLE 22 was obtained. HRMS calculated for $C_{31}H_{33}N_4O_3Cl$: 544.2241: found 545.2307 [(M+H)$^+$ form].

3-[[4-hydroxy-1-(trans-2-phenylcyclohexanecarbonyl)-4-piperidyl]methyl]-7-(3-thienyl)pyrrolo[2,3-d]pyrimidin-4-one (Example 23)

Using General Procedure 4 starting from Preparation R2f and Preparation R1c as reagents. EXAMPLE 23 was obtained. HRMS calculated for $C_{29}H_{32}N_4O_3S$: 516.2195: found 517.2267 [(M+H)$^+$ form].

3-[[4-hydroxy-1-[trans-2-phenyltetrahydropyran-3-carbonyl]-4-piperidyl]methyl]-7-(4-methoxyphenyl)pyrrolo[2,3-d]pyrimidin-4-one (Example 24)

Using Step 3 of General Procedure 3 starting from Preparation R3b and 2-phenyltetrahydropyran-3-carboxylic acid as reagents. EXAMPLE 24 was obtained. HRMS calculated for $C_{31}H_{34}N_4O_5$: 542.2529: found 543.26 [(M+H)$^+$ form].

3-[[4-hydroxy-1-[(trans-2-phenyltetrahydropyran-3-carbonyl]-4-piperidyl]methyl]-7-phenyl-pyrrolo[2,3-d]pyrimidin-4-one, enantiomer 1 (Example 25)

and

3-[[4-hydroxy-1-[trans-2-phenyltetrahydropyran-3-carbonyl]-4-piperidyl]methyl]-7-phenyl-pyrrolo[2,3-d]pyrimidin-4-one, enantiomer 2 (Example 26)

Using Step 3 of General Procedure 3 starting from Preparation R3e and 2-phenyltetrahydropyran-3-carboxylic acid as reagents. EXAMPLE 25 and EXAMPLE 26 were obtained separately by chiral chromatography.

EXAMPLE 25: HRMS calculated for $C_{30}H_{32}N_4O_4$: 512.2424: found 513.249 [(M+H)$^+$ form EXAMPLE 26: HRMS calculated for $C_{30}H_{32}N_4O_4$: 512.2424: found 513.2501 [(M+H)$^+$ form].

3-[[4-hydroxy-1-[trans-1-methyl-6-oxo-2-phenyl-piperidine-3-carbonyl]-4-piperidyl]methyl]-7-phenyl-pyrrolo[2,3-d]pyrimidin-4-one, enantiomer 1 (Example 27)

and

3-[[4-hydroxy-1-[trans-1-methyl-6-oxo-2-phenyl-piperidine-3-carbonyl]-4-piperidyl]methyl]-7-phenyl-pyrrolo[2,3-d]pyrimidin-4-one, enantiomer 2 (Example 28)

Using Step 3 of General Procedure 3 starting from Preparation R3e and trans-1-methyl-6-oxo-2-phenyl-piperidine-3-carboxylic acid a reagents, EXAMPLE 27 and EXAMPLE 28 were obtained separately by chiral chromatography.

EXAMPLE 27: HRMS calculated for $C_{31}H_{33}N_5O_4$: 339.2532: found 540.2606 [(M+H)$^+$ form].

EXAMPLE 28: HRMS calculated for $C_{31}H_{33}N_5O_4$: 539.2532: found 540.2607 [(M+H)$^+$ form].

3-[[1-[trans-5,5-difluoro-2-phenyl-cyclohexanecarbonyl]-4-hydroxy-4-piperidyl]methyl]-7-(4-methoxyphenyl)pyrrolo[2,3-d]pyrimidin-4-one, enantiomer 1 (Example 29)

and

3-[[1-[trans-5,5-difluoro-2-phenyl-cyclohexanecarbonyl]-4-hydroxy-4-piperidyl]methyl]-7-(4-methoxyphenyl)pyrrolo[2,3-d]pyrimidin-4-one, enantiomer 2 (Example 30)

Using Step 3 of General Procedure 3 starting from Preparation R3b and Preparation R4ak as reagents. EXAMPLE 29 and EXAMPLE 36 were obtained separately by chiral chromatography.

EXAMPLE 29: HRMS calculated for $C_{32}H_{34}N_4O_4F_2$: 576.2548: found 577.2624 [(M+H)+ form].

EXAMPLE 30: HRMS calculated for $C_{32}H_{34}N_4O_4F_2$: 576.2548: round 5771619 [(M+H)$^+$ form].

3-[[1-[trans-5,5-difluoro-2-phenyl-cyclohexanecarbonyl]-4-hydroxy-4-piperidyl]methyl]-7-phenyl-pyrrolo[2,3-d]pyrimidin-4-one, enantiomer 1 (Example 31)

and

3-[[1-[trans-5,5-difluoro-2-phenyl-cyclohexanecarbonyl]-4-hydroxy-4-piperidyl]methyl]-7-phenyl-pyrrolo[2,3-d]pyrimidin-4-one, enantiomer 2 (Example 32)

Using Step 3 of General Procedure 3 starting from Preparation R3e and Preparation R4ak as reagents, EXAMPLE 31 and EXAMPLE 32 were obtained separately by chiral chromatography.

EXAMPLE 31: HRMS calculated for $C_{31}H_{32}N_4O_3F_2$: 546.2443: found 547.2516 [(M+H)$^+$ form].

EXAMPLE 32: HRMS calculated for $C_{31}H_{32}N_4O_3F_2$: 546.2443: found 547.2519 [(M+H)$^+$ form].

3-[[1-(trans-4,4-difluoro-2-phenyl-cyclohexanecarbonyl)-4-hydroxy-4-piperidyl]methyl]-7-(4-methoxyphenyl)pyrrolo[2,3-d]pyrimidin-4-one, enantiomer 1 (Example 33)

and

3-[[1-[trans-4,4-difluoro-2-phenyl-cyclohexanecarbonyl]-4-hydroxy-4-piperidyl]methyl]-7-(4-methoxyphenyl)pyrrolo[2,3-d]pyrimidin-4-one, enantiomer 2 (Example 34)

Using Step 3 of General Procedure 3 starting from Preparation R3b and Preparation R4ah as reagents. EXAMPLE 33 and EXAMPLE 34 were obtained separately by chiral chromatography.

EXAMPLE 33: HRMS calculated for $C_{32}H_{34}N_4O_4F_2$: 576.2548: found 577.2619 [(M+H)$^+$ form].

EXAMPLE 34: HRMS calculated for $C_{32}H_{34}N_4O_4F_2$: 576.2548: found 577.2623 [(M+H)$^+$ form].

3-[[1-[trans-4,4-difluoro-2-phenyl-cyclohexanecarbonyl]-4-hydroxy-4-piperidyl]methyl]-7-phenyl-pyrrolo[2,3-d]pyrimidin-4-one, enantiomer 1 (Example 35)

and

3-[[1-[trans-4,4-difluoro-2-phenyl-cyclohexanecarbonyl]-4-hydroxy-4-piperidyl]methyl]-7-phenyl-pyrrolo[2,3-d]pyrimidin-4-one, enantiomer 2 (Example 36)

Using Step 3 of General Procedure 3 starting from Preparation R3e and Preparation R4ah as reagents EXAMPLE 35 and EXAMPLE 36 were obtained separately by chiral chromatography.

EXAMPLE 35: HRMS calculated for $C_{31}H_{32}N_5O_3F_2$: 546.2443: found 547.2519 [(M+H)$^+$ form].

EXAMPLE 36: HRMS calculated for $C_{31}H_{32}N_4O_3F_2$: 546.2443: found 547.2518 [(M+H)$^+$ form].

3-[[1-[5-fluoro-2-phenyl-cyclohexanecarbonyl]-4-hydroxy-4-piperidyl]methyl]-7-phenyl-pyrrolo[2,3-d]pyrimidin-4-one (Example 37)

Using Step 3 of General Procedure 3 starting from Preparation R3e and Preparation R4h as reagents. EXAMPLE 37 was obtained. HRMS calculated for $C_{31}H_{33}N_4O_3F$: 528.2537: found 329.2602 [(M+H)$^+$ form].

3-[[4-hydroxy-1-[trans-1-methyl-6-oxo-2-phenyl-piperidine-3-carbonyl]-4-piperidyl]methyl]-7-methyl-pyrrolo[2,3-d]pyrimidin-4-one, enantiomer 1 (Example 38)

and

3-[[4-hydroxy-1-[trans-1-methyl-6-oxo-2-phenyl-piperidine-3-carbonyl]-4-piperidyl]methyl]-7-methyl-pyrrolo[2,3-d]pyrimidin-4-one, enantiomer 2 (Example 39)

Using Step 3 of General Procedure 3 starting from Preparation R3d and trans-1-methyl-6-oxo-2-phenyl-piperidine- 3-carboxylic acid as reagents. EXAMPLE 3 and EXAMPLE 39 were obtained separately by chiral separation.

EXAMPLE 38: HRMS calculated for $C_{26}H_{31}N_5O_4$: 477.2376: found 478.2456 [(M+H)$^+$ form].

EXAMPLE 39: HRMS calculated for $C_{26}H_{31}N_5O_4$: 477.2376: found 478.2447 [(M+H)$^+$ form].

3-[[1-[trans-2-(4-fluorophenyl)cyclohexanecarbonyl]-4-hydroxy-4-piperidyl]methyl]-7-(4-methoxyphenyl)pyrrolo[2,3-d]pyrimidin-4-one, enantiomer 1 (Example 40)

and

3-[[1-[trans-2-(4-fluorophenyl)cyclohexanecarbonyl]-4-hydroxy-4-piperidyl]methyl]-7-(4-methoxyphenyl)pyrrolo[2,3-d]pyrimidin-4-one, enantiomer 2 (Example 41)

Using Step 3 of General Procedure 3 starting from Preparation R3b and 2-(4-fluorophenyl)cyclohexanecarboxylic acid as reagents. EXAMPLE 40 and EXAMPLE 41 were obtained separately by chiral chromatography.

EXAMPLE 40: HRMS calculated for $C_{32}H_{35}N_4O_4F$: 558.2642: found 559.2722 [(M+H)$^+$ form].

EXAMPLE 41: HRMS calculated for $C_{32}H_{35}N_4O_4F$: 559.2642: found 559.2722 [(M+H)$^+$ form].

3-[[1-[(trans-2-(4-fluorophenyl)cyclohexanecarbonyl]-4-hydroxy-4-piperidyl]methyl]-7-phenyl-pyrrolo[2,3-d]pyrimidin-4-one, enantiomer 2 (Example 42)

and

3-[[1-[trans-2-(4-fluorophenyl)cyclohexanecarbonyl]-4-hydroxy-4-piperidyl]methyl]-7-phenyl-pyrrolo[2,3-d]pyrimidin-4-one, enantiomer 1 (Example 43)

Using Step 3 of General Procedure 3 starting from Preparation R3e and 2-(4-fluorophenyl)cyclohexanecarboxylic acid as reagents. EXAMPLE 42 and EXAMPLE 43 were obtained separately by chiral chromatography.

EXAMPLE 42: HRMS calculated for $C_{31}H_{33}N_4O_3F$: 528.2537: found 529.2625 [(M+H)$^+$ form].

EXAMPLE 43: HRMS calculated for $C_{31}H_{33}N_4O_3F$: 528.2537: found 529.2615 [(M+H)$^+$ form].

3-[[4-hydroxy-1-[trans-2-phenyltetrahydropyran-3-carbonyl]-4-piperidyl]methyl]-7-(4-methoxyphenyl)pyrrolo[2,3-d]pyrimidin-4-one, enantiomer 1 (Example 44)

and

3-[[4-hydroxy-1-[trans-2-phenyltetrahydropyran-3-carbonyl]-4-piperidyl]methyl]-7-(4-methoxyphenyl)pyrrolo[2,3-d]pyrimidin-4-one, enantiomer 2 (Example 45)

Using Step 3 of General Procedure 3 starting from Preparation R3b and 2-phenyltetrahydropyran-3-carboxylic acid as reagents, EXAMPLE 44 and EXAMPLE 45 were obtained separately by chiral chromatography.

EXAMPLE 44: HRMS calculated for $C_{31}H_{34}N_4O_5$: 542.2529: found 543.2614 [(M+H)$^+$ form].

EXAMPLE 45: HRMS calculated for $C_{31}H_{34}N_4O_5$: 542.2529: found 543.2589 [(M+H)$^+$ form].

3-[[4-hydroxy-1-[trans-2-phenyltetrahydrofuran-3-carbonyl]-4-piperidyl]methyl]-7-phenyl-pyrrolo[2,3-d]pyrimidin-4-one (Example 46)

Using Step 3 of General Procedure 3 starting from Preparation Re and trans-2-phenyltetrahydrofuran-3-carboxylic acid as reagents. EXAMPLE 46 was obtained. HRMS calculated for $C_{29}H_{30}N_4O_4$: 49.2267: found 499.2336 [(M+H)$^+$ form].

3-[[4-hydroxy-1-[trans-2-imidazol-1-ylcyclohexanecarbonyl]-4-piperidyl]methyl]-7-(4-methoxyphenyl)pyrrolo[2,3-d]pyrimidin-4-one, enantiomer 1 (Example 47)

and

3-[[4-hydroxy-1-[trans-2-imidazol-1-ylcyclohexanecarbonyl]-4-piperidyl]methyl]-7-(4-methoxyphenyl)pyrrolo[2,3-d]pyrimidin-4-one, enantiomer 2 (Example 48)

Using Step 3 of General Procedure 3 starting from Preparation R3b and trans-2-imidazol-1-ylcyclohexanecarboxylic acid as reagents. EXAMPLE 47 and EXAMPLE 48 were obtained separately by chiral chromatography.

EXAMPLE 47: HRMS calculated for $C_{29}H_{34}N_6O_4$: 530.2642: found 531.2708 [(M+H)$^+$ form].

EXAMPLE 48: HRMS calculated for $C_{29}H_{34}N_6O_4$: 530.2642: found 531.2718 [(M+H)$^+$ form].

3-[[4-hydroxy-1-[trans-2-imidazol-1-ylcyclohexanecarbonyl]-4-piperidyl]methyl]-7-phenyl-pyrrolo[2,3-d]pyrimidin-4-one enantiomer 1 (Example 49)

and

3-[[4-hydroxy-1-[trans-2-imidazol-1-ylcyclohexanecarbonyl]-4-piperidyl]methyl]-7-phenyl-pyrrolo[2,3-d]pyrimidin-4-one, enantiomer 2 (Example 50)

Using Step 3 of General Procedure 3 starting from Preparation R3e and trans-2-imidazol-1-ylcyclohexanecarbonylic acid as reagents EXAMPLE 49 and EXAMPLE 50 were obtained separately by chiral chromatography.

EXAMPLE 49: HRMS calculated for $C_{28}H_{32}N_6O_3$: 500.2536: found 501.2612 [(M+H)$^+$ form].

EXAMPLE 50: HRMS calculated for $C_{28}H_{32}N_6O_3$: 500.2536: found 501.262 [(M+H)$^+$ form].

3-[[1-[trans-3,3-difluo-2-phenyl-cyclohexanecarbonyl]-4-hydroxy-4-piperidyl]methyl]-7-phenyl-pyrrolo[2,3-d]pyrimidin-4-one, enantiomer 1 (Example 51)

Using Step 3 of General Procedure 3 starting from Preparation Re and Preparation R4x as reagents. EXAMPLE 51 was obtained. HRMS calculated for $C_{31}H_{32}N_4O_3F_2$: 546.2443; found 547.2507 [(M+H)$^+$ form].

3-[[1-[trans-3,3-difluoro-2-phenyl-cyclohexanecarbonyl]-4-hydroxy-4-piperidyl]methyl]-7-phenyl-pyrrolo[2,3-d]pyrimidin-4-one, enanatiomer 2 (Example 52)

Using Step 3 of General Procedure 3 starting from Preparation Re and Preparation R4y as reagents, EXAMPLE 52 was obtained. HRMS calculated for $C_{31}H_{32}N_4O_3F_2$: 546.2443: found 547.2505 [(M+H)+ form].

(1S,2S,3R or 1R,2R,3S)-3-[[4-hydroxy-1-[3-hydroxy-2-phenyl-cyclohexanecarbonyl]-4-piperidyl]methyl]-7-phenyl-pyrrolo[2,3-d]pyrimidin-4-one, enantiomer 1 (Example 53)

Using Step 3 of General Procedure 3 starting from Preparation R3e and Preparation R4d as reagents. EXAMPLE 53 was obtained. HRMS calculated for $C_{31}H_{34}N_4O_4$: 526.258: found 527.2657 [(M+H)+ form].

(1S,2S,3S or 1R,2R,3R)-3-[[4-hydroxy-1-[3-hydroxy-2-phenyl-cyclohexanecarbonyl]-4-piperidyl]methyl]-7-phenyl-pyrrolo[2,3-d]pyrimidin-4-one, enantiomer 1 (Example 54)

Using Step 3 of General Procedure 3 starting from Preparation Re and Preparation R4e as reagents. EXAMPLE 54 was obtained. HRMS calculated for $C_{31}H_{34}N_4O_4$: 526.258: found 527.2672 [(M+H)+ form].

(1S,2S,3R or 1R,2R,3S)-3-[[4-hydroxy-1-[3-hydroxy-2-phenyl-cyclohexanecarbonyl]-4-piperidyl]methyl]-7-phenyl-pyrrolo[2,3-d]pyrimidin-4-one, enantiomer 2 (Example 55)

Using Step 3 of General Procedure 3 starting from Preparation R3e and Preparation R4f 3 as reagents. EXAMPLE 55 was obtained. HRMS calculated for $C_{31}H_{34}N_4O_4$: 26.258: found 527.2668 [(M+H)+ form].

(1S,2S,3S or 1R,2R,3R)-3-[[4-hydroxy-1-[3-hydroxy-2-phenyl-cyclohexanecarbonyl]-4-piperidyl]methyl]-7-phenyl-pyrrolo[2,3-d]pyrimidin-4-one, enantiomer 2 (Example 56)

Using Step 3 of General Procedure 3 starting from Preparation R3e and Preparation R4g as reagents. EXAMPLE 56 was obtained. HRMS calculated for $C_{31}H_{34}N_4O_4$: 526.258: found 527.2659 [(M+H)+ form].

3-[[4-hydroxy-1-[trans-2-(1-methylimidazol-2-yl)cyclohexanecarbonyl]-4-piperidyl]methyl]-7-phenyl-pyrrolo[2,3-d]pyrimidin-4-one, enantiomer 1 (Example 57)

and

3-[[4-hydroxy-1-[trans-2-(1-methylimidazol-2-yl)cyclohexanecarbonyl]-4-piperidyl]methyl]-7-phenyl-pyrrolo[2,3-d]pyrimidin-4-one, enantiomer 2 (Example 58)

Using Step 3 of General Procedure 3 starting from Preparation R3e and trans-2-(1-methylimidazol-2-yl)cyclohexanecarboxylic acid as reagents. EXAMPLE 57 and EXAMPLE 58 were obtained separately by chiral chromatography.
EXAMPLE 57: HRMS calculated for $C_{29}H_{34}N_6O_3$: 514.2692: found 515.2768 [(M+H)+ form].
EXAMPLE 58: HRMS calculated for $C_{29}H_{34}N_6O_3$: 514.2692: found 515.2771 [(M+H)+ form].

3-[[4-hydroxy-1-[trans-2-methyl-6-(2-thienyl)cyclohex-2-ene-1-carbonyl]-4-piperidyl]methyl]-7-(4-methoxyphenyl)pyrrolo[2,3-d]pyrimidin-4-one, enantiomer 1 (Example 59)

and

3-[[4-hydroxy-1-[trans-2-methy-6-(2-thienyl)cyclohex-2-ene-1-carbonyl]-4-piperidyl]methyl]-7-(4-methoxyphenyl)pyrrolo[2,3-d]pyrimidin-4-one, enantiomer 2 (Example 60)

Using Step 3 of General Procedure 3 starting from Preparation Rb and Preparation R4s as reagents. EXAMPLE 59 and EXAMPLE 60 were obtained separately by chiral chromatography.
EXAMPLE 9: HRMS calculated for $C_{31}H_{34}N_4O_4S$: 55.2301: found 559.2314 [(M+H)− form].
EXAMPLE 60: HRMS calculated for $C_{31}H_{34}N_4O_4S$: 558.2301: found 559.2379 [(M+H)+ form].

3-[[4-hydroxy-1-[trans-2-methyl-6-(3-thienyl)cyclohex-2-ene-1-carbonyl]-4-piperidyl]methyl]-7-(4-methoxyphenyl)pyrrolo[2,3-d]pyrimidin-4-one, enantiomer 1 (Example 61)

and

3-[[4-hydroxy-1-[trans-2-methyl-6-(3-thienyl)cyclohex-2-ene-1-carbonyl]-4-piperidyl]methyl]-7-(4-methoxyphenyl)pyrrolo[2,3-d]pyrimidin-4-one, enantiomer 2 (Example 62)

Using Step 3 of General Procedure 3 starting from Preparation R3b and Preparation R4 as reagents. EXAMPLE 61 and EXAMPLE 62 were obtained separately by chiral chromatography.
EXAMPLE 61: HRMS calculated for $C_{31}H_{34}N_4O_4S$: 558.2301: found 559.2379 [(M+H)+ form].
EXAMPLE 62: HRMS calculated for $C_{31}H_{34}N_4O_4S$: 558.2301: found 559.2371 [(M+H)+ form].

3-[[4-hydroxy-1-[trans-2-(2-oxopyrrolidin-1-yl)cyclohexanecarbonyl]-4-piperidyl]methyl]-7-(4-methoxyphenyl)pyrrolo[2,3-d]pyrimidin-4-one, enantiomer 2 (Example 63)

and

3-[[4-hydroxy-1-[trans-2-(2-oxopyrrolidin-1-yl)cyclohexanecarbonyl]-4-piperidyl]methyl]-7-(4-methoxyphenyl)pyrrolo[2,3-d]pyrimidin-4-one, enantiomer 1 (Example 64)

Using Step 3 of General Procedure 3 starting from Preparation R3b and trans-2-(2-oxopyrrolidin-1-yl)cyclohexanecarboxylic acid as reagents. EXAMPLE 63 and EXAMPLE 64 were obtained separately by chiral chromatography.
EXAMPLE 63: HRMS calculated for $C_{30}H_{37}N_5O_5$: 547.2795: found 548.2867 [(M+H)+ form].
EXAMPLE 64: HRMS calculated for $C_{30}H_{37}N_5O_5$: 547.2795: found 548.287 [(M+H)+ form].

3-[[4-hydroxy-1-trans-2-(2-oxopyrrolidin-1-yl)cyclohexanecarbonyl-4-piperidyl]methyl]-7-phenyl-pyrrolo[2,3-d]pyrimidin-4-one, enantiomer 1 (Example 65)

and

3-[[4-hydroxy-1-[trans-2-oxopyrrolidin-1-yl)cyclohexanecarbonyl]-4-piperidyl]methyl]-7-phenyl-pyrrolo[2,3-d]pyrimidin-4-one, enantiomer 2 (Example 66)

Using Step 3 of General Procedure 3 starting from Preparation R3e and trans-2-(2-oxopyrrolidin-1-yl)cyclohexanecarboxylic acid as reagents. EXAMPLE 65 and EXAMPLE 66 were obtained separately by chiral chromatography.
EXAMPLE 65: HRMS calculated for $C_{29}H_{35}N_5O_4$: 517.269: found 518.2767 [(M+H)$^+$ form].
EXAMPLE 66: HRMS calculated for $C_{29}H_{35}N_5O_4$: 517.2689: found 518.2755 [(M+H)$^+$ form].

7-[4-(hydroxymethyl)phenyl]-3-[[4-hydroxy-1-[trans-2-(2-oxopyrrolidin-1-yl)cyclohexanecarbonyl]-4-piperidyl]methyl]pyrrolo[2,3-d]pyrimidin-4-one, enantiomer 1 (Example 67)

and

7-[4-(hydroxymethyl)phenyl]-3-[[4-hydroxy-1-[trans-2-(2-oxopyrrolidin-1-yl)cyclohexanecarbonyl]-4-piperidyl]methyl]pyrrolo[2,3-d]pyrimidin-4-one, enantiomer 2 (Example 68)

Using Step 3 of General Procedure 3 starting from Preparation R3g and trans-2-(2-oxopyrrolidin-1-yl)cyclohexanecarboxylic acid as reagents. EXAMPLE 67 and EXAMPLE 68 were obtained separately by chiral chromatography.
EXAMPLE 67: HRMS calculated for $C_{30}H_{37}N_5O_5$: 547.2795: found 54.2872 [(M+H)$^+$ form].
EXAMPLE 68: HRMS calculated for $C_{30}H_{37}N_5O_5$: 547.2795: found 54.2864 [(M+H)$^+$ form].

3-[[4-hydroxy-1-trans-2-(1-methylimidazol-2-yl)cyclohexanecarbonyl]-4-piperidyl]methyl-7-(4-methoxyphenyl)pyrrolo[2,3-d]pyrimidin-4-one, enantiomer 1 (Example 69)

and

3-[[4-hydroxy-1-[trans-2-(1-methylimidazol-2-yl)cyclohexanecarbonyl]-4-piperidyl]methyl]-7-(4-methoxyphenyl)pyrrolo[2,3-d]pyrimidin-4-one, enantiomer 2 (Example 70)

Using Step 3 of General Procedure 3 starting from Preparation R3b and trans-2-(1-methylimidazol-2-yl)cyclohexanecarboxylic acid as reagents, EXAMPLE 69 and
EXAMPLE 70 were obtained separately by chiral chromatography.
EXAMPLE 69: HRMS calculated for $C_{30}H_{36}N_6O_4$: 544.2798: found 545.2878 [(M+H)$^+$ form].
EXAMPLE 70: HRMS calculated for $C_{30}H_{36}N_6O_4$: 544.2798: found 545.2874 [(M+H)$^+$ form].

3-[[1-[trans-4,4-difluoro-2-(2-thienyl)cyclohexanecarbonyl]-4-hydroxy-4-piperidyl]methyl]-7-phenyl-pyrrolo[2,3-d]pyrimidin-4-one (Example 71)

Using Step 3 of General Procedure 3 starting from Preparation R3e and Preparation R4aj as reagents. EXAMPLE 71 was obtained. HRMS calculated for $C_{29}H_{30}N_4O_3F_2S$: 552.2007: found 553.2077 [(M+H)$^+$ form].

3-[[1-[trans-4,4-difluoro-2-(2-thienyl)cyclohexanecarbonyl]-4-hydroxy-4-piperidyl]methyl]-7-(4-methoxyphenyl)pyrrolo[2,3-d]pyrimidin-4-one, enantiomer 1 (Example 72)

and

3-[[1-[trans-4,4-difluoro-2-(2-thienyl)cyclohexanecarbonyl]-4-hydroxy-4-piperidyl]methyl]-7-(4-methoxyphenyl)pyrrolo[2,3-d]pyrimidin-4-one, enantiomer 2 (Example 73)

Using Step 3 of General Procedure 3 starting from Preparation R3b and Preparation R4aj as reagents. EXAMPLE 72 and EXAMPLE 73 were obtained separately by chiral chromatography.
EXAMPLE 72: HRMS calculated for $C_{30}H_{32}F_2N_4O_4S$: 582.2112: found 583.2204 [(M+H)$^+$ form].
EXAMPLE 73: HRMS calculated for $C_{30}H_{32}N_4O_4F_2S$: 582.2112: found 583.2184 [(M+H)$^+$ form].

3-[[1-[trans-4,4-difluoro-2-(3-fury)cyclohexanecarbonyl]-4-hydroxy-4-piperidyl]methyl]-7-(4-methoxyphenyl)pyrrolo[2,3-d]pyrimidin-4-one, enantiomer 1 (Example 74)

and

3-[[1-[trans-4,4-difluoro-2-(3-furyl)cyclohexanecarbonyl]-4-hydroxy-4-piperidyl]methyl]-7-(4-methoxyphenyl)pyrrolo[2,3-d]pyrimidin-4-one, enantiomer 2 (Example 75)

Using Step 3 of General Procedure 3 starting from Preparation R3b and Preparation R4aa as reagents. EXAMPLE 74 and EXAMPLE 75 were obtained separately by chiral chromatography.
EXAMPLE 74: HRMS calculated for $C_{30}H_{32}F_2N_4O_5$: 566.2341: found 567.2413 [(M+H)$^+$ form].
EXAMPLE 75: HRMS calculated for $C_{30}H_{32}F_2N_4O_5$: 566.2341: found 567.2429 [(M+H)$^+$ form].

7-chloro-3-[[1-[trans-4,4-difluoro-2-oxazol-5-yl-cyclohexanecarbonyl]-4-hydroxy-4-piperidyl]methyl]thieno[3,4-d]pyrimidin-4-one (Example 76)

Using Step 3 of General Procedure 3 starting from Preparation R3 and Preparation R4ag as reagents. EXAMPLE 76 was obtained. HRMS calculated for $C_{22}H_{23}ClF_2N_4O_4S$: 512.1097: found 513.1172 [(M+H)$^+$ form].

3-[[1-[trans-4,4-difluoro-2-oxazol-4-yl-cyclohexanecarbonyl]-4-hydroxy-4-piperidyl]methyl]-7-[4-(hydroxymethyl)phenyl]thieno[3,4-d]pyrimidin-4-one (Example 77)

Using Step 3 of General Procedure 3 starting from Preparation R3h and Preparation R4af as reagents, the corresponding halogenated compound was obtained which, using General Procedure 5, was reacted with 4-(hydroxymethyl)phenylboronic acid to give EXAMPLE 77. HRMS calculated for $C_{29}H_{30}F_2N_4O_5S$: 584.1905: found 585.1992 [(M+H)$^+$ form].

3-[[1-[trans-5,5-difluoro-2-phenyl-cyclohexanecarbonyl]-4-hydroxy-4-piperidyl]methyl]-7-phenyl-thieno[3,4-d]pyrimidin-4-one, enantiomer 1 (Example 73)

and

3-[[1-[trans-5,5-difluoro-2-phenyl-cyclohexanecarbonyl]-4-hydroxy-4-piperidyl]methyl]-7-phenyl-thieno[3,4-d]pyrimidin-4-one, enantiomer 2 (Example 79)

Using Step 3 of: General Procedure 3 starting from Preparation R3h and Preparation R4ak as reagents, the corresponding halogenated compound was obtained which, using General Procedure 5, was reacted with phenylboronic acid to give EXAMPLE 78 and EXAMPLE 79 separately by chiral chromatography.
EXAMPLE 78: HRMS calculated for $C_{31}H_{31}F_2N_3O_3S$: 563.2054: found 564.212 [(M+H)$^+$ form].
EXAMPLE 79: HRMS calculated for $C_{31}H_{31}F_2N_3O_3S$: 563.2054: found 564.2118 [(M+H)$^+$ form].

3-[[1-[trans-2-(1-ethylpyrazol-4-yl)-4,4-difluoro-cyclohexanecarbonyl]-4-hydroxy-4-piperidyl]methyl]-7-phenyl-thieno[3,4-d]pyrimidin-4-one, enantiomer 1 (Example 80)

and

3-[[1-[trans-2-(1-ethylpyrazol-4-yl)-4,4-difluoro-cyclohexanecarbonyl]-4-hydroxy-4-piperidyl]methyl]-7-phenyl-thieno[3,4-d]pyrimidin-4-one, enantiomer 2 (Example 81)

Using Step 3 of General Procedure 3 starting from Preparation R3h and Preparation R4l as reagents, the corresponding halogenated compound was obtained which, using General Procedure 5, was reacted with phenylboronic acid to give EXAMPLE 80 and EXAMPLE 81 separately by chiral chromatography.
EXAMPLE 80: HRMS calculated for $C_{30}H_{33}F_2N_5O_3$: 581.2272: found 582.2336 [(M+H)$^+$ form].
EXAMPLE 81: HRMS calculated for $C_{30}H_{33}F_2N_5O_3$: 581.2272: found 582.2346 [(M+H)$^+$ form].

3-[[1-[trans-4,4-difluoro-2-thiazol-4-yl-cyclohexanecarbonyl]-4-hydroxy-4-piperidyl]methyl]-7-phenyl-thieno[3,4-d]pyrimidin-4-one, enantiomer 1 (Example 82)

and

3-[[1-[trans-4,4-difluoro-2-thiazol-4-yl-cyclohexanecarbonyl]-4-hydroxy-4-piperidyl]methyl]-7-phenyl-thieno[3,4-d]pyrimidin-4-one, enantiomer 2 (Example 83)

Using Step 3 of General Procedure 3 starting from Preparation R3h and Preparation R4ai as reagents, the corresponding halogenated compound was obtained which, using General Procedure 5, was reacted with phenylboronic acid to give EXAMPLE 82 and EXAMPLE 83 separately by chiral chromatography.
EXAMPLE 82: HRMS calculated for $C_{28}H_{28}F_2N_4O_3S_2$: 570.1571: found 571.1638 [(M+H)$^+$ form].
EXAMPLE 83: HRMS calculated for $C_{28}H_{28}F_2N_4O_3S_2$: 570.1571: found 571.163 [(M+H)$^+$ form].

3-[[1-[trans-4,4-difluoro-2-(4-pyridyl)cyclohexanecarbonyl]-4-hydroxy-4-piperidyl]methyl]-7-phenyl-thieno[3,4-d]pyrimidin-4-one (Example 34)

Using Step 3 of General Procedure 3 starting from Preparation R3b and Preparation R4ac as reagents, the corresponding halogenated compound was obtained which, using General Procedure 5, was reacted with phenylboronic acid to give EXAMPLE 84. HRMS calculated for $C_{30}H_{30}F_2N_4O_3S$: 564.2007: found 565.2084 [(M+H)$^+$ form].

3-[[1-[trans-4,4-difluoro-2-(2-furyl)cyclohexanecarbonyl]-4-hydroxy-4-piperidyl]methyl]-7-phenyl-thieno[3,4d]pyrimidin-4-one, enantiomer 1 (Example 85)

and

3-[[1-[trans-4,4-difluoro-2-(2-furyl)cyclohexanecarbonyl]-4-hydroxy-4-piperidyl]methyl]-7-phenyl-thieno[3,4-d]pyrimidin-4-one, enantiomer 2 (Example 86)

Using Step 3 of General Procedure 3 starting from Preparation R3 and Preparation R4z as reagents, the corresponding halogenated compound was obtained which, using General Procedure 5, was reacted with phenylboronic acid to give EXAMPLE 85 and EXAMPLE 86 separately by chiral chromatography.
EXAMPLE 35: HRMS calculated for $C_{29}H_{29}F_2N_3O_4S$: 553.1947: found 554.1923 [(M+H)$^+$ form].
EXAMPLE 86: HRMS calculated for $C_{29}H_{29}F_2N_3O_4S$: 553.1147: found 554.1921 [(M+H)$^+$ form].

3-[[1-[trans-4,4-difluoro-2-(3-thienyl)cyclohexanecarbonyl]-4-hydroxy-4-piperidyl]methyl]-7-phenyl-thieno[3,4-d]pyrimidin-4-one, enantiomer 1 (Example 87)

and

3-[[1-[trans-4,4-difluoro-2-(3-thienyl)cyclohexanecarbonyl]-4-hydroxy-4-piperidyl]methyl]-7-phenyl-thieno[3,4-d]pyrimidin-4-one, enantiomer 2 (Example 88)

Using Step 3 of General Procedure 3 starting from Preparation R3h and Preparation R4ab as reagents, the corresponding halogenated compound was obtained which, using General Procedure 5, was reacted with phenylboronic acid to give EXAMPLE 87 and EXAMPLE 88 separately by chiral chromatography.
EXAMPLE 87: HRMS calculated for $C_{29}H_{29}F_2N_3O_3S_3$: 569.1619: found 570.1693 [(M+H)$^+$ form].

EXAMPLE 88: HRMS calculated for $C_{29}H_{29}F_2N_3O_3S_2$: 569.1619: found 570.1695 [(M+H)$^+$ form].

3-[[1-[trans-4,4-difluoro-2-(5-methyl-3-thienyl)cyclohexanecarbonyl]-4-hydroxy-4-piperidyl]methyl]-7-phenyl-thieno[3,4-d]pyrimidin-4-one, enantiomer 1 (Example 89)

and

3-[[1-[trans-4,4-difluoro-2-(S-methyl-3-thienyl)cyclohexanecarbonyl]-4-hydroxy-4-piperidyl]methyl]-7-phenyl-thieno[3,4-d]pyrimidin-4-one, enantiomer 2 (Example 90)

Using Step 3 of General Procedure 3 starting from Preparation R3h and Preparation R4ad as reagents, the corresponding halogenated compound was obtained which, using General Procedure 5, was reacted with phenylboronic acid to give EXAMPLE 89 and EXAMPLE 90 separately by chiral chromatography.
EXAMPLE 89: HRMS calculated for $C_{30}H_{31}F_2N_3O_3S_2$: 583.1775: found 584.1847 [(M+H)$^+$ form].
EXAMPLE 90: HRMS calculated for $C_{30}H_{31}F_2N_3O_3S_2$: 583.1775: found 584.15 [(M+H)$^+$ form].

3-[[4-hydroxy-1-(trans-2-phenylcyclohexanecarbonyl)-4-piperidyl]methyl]thieno[2,3-d]pyrimidin-4-one (Example 91)

Using General Procedure 4 starting from 3H-thieno[2,3-d]pyrimidin-4-one and Preparation R1c as reagents. EXAMPLE 91 was obtained. HRMS calculated for $C_{25}H_{29}N_3O_3S$: 451.193: found 452.1996 [(M+H)$^+$ form].

3-[[4-hydroxy-1-(trans-2-phenylcyclohexanecarbonyl)-4-piperidyl]methyl]-7H-pyrrolo[2,3-d]pyrimidin-4-one (Example 92)

Using Step 3 of General Procedure 3 starting from Preparation R3c and trans-2-phenylcyclohexanecarboxylic acid as reagents. EXAMPLE 92 was obtained. HRMS calculated for $C_{25}H_{30}N_4O_3$: 434.2318: found 435.2403 [(M+H)$^+$ form].

3-[[4-hydroxy-1-(trans-2-phenylcyclohexanecarbonyl)-4-piperidyl]methyl]pyrido[3,2-d]pyrimidin-4-one (Example 93)

Using Step 3 of General Procedure 3 starting from Preparation R3f and trans-2-phenylcyclohexanecarboxylic acid as reagents. EXAMPLE 93 was obtained. HRMS calculated for $C_{26}H_{30}N_4O_3$: 446.2311: found 447.2397 [(M+H)$^+$ form].

3-[[4-hydroxy-1-(trans-2-phenylcyclohexanecarbonyl)-4-piperidyl]methyl]-6-[(4-methoxyphenyl)methylamino]pyrido[3,2-d]pyrimidin-4-one (Example 94)

Using Step 3 of General Procedure 3 starting from Preparation R3a and trans-2-phenylcyclohexanecarboxylic acid as reagents, EXAMPLE 94 was obtained. HRMS calculated for $C_{34}H_{39}N_5O_4$: 581.3002: found 582.3049 [(M+H)$^+$ form].

3-[[1-[trans-4,4-difluoro-2-[5-(trifluoromethyl)-3-thienyl]cyclohexanecarbonyl]-4-hydroxy-4-piperidyl]methyl]-7-phenyl-thieno[3,4-d]pyrimidin-4-one (Example 95)

Using Step 3 of General Procedure 3 starting from Preparation R3h and Preparation R4ae as reagents, the corresponding halogenated compound was obtained which, using General Procedure 5, was reacted with phenylboronic acid to give EXAMPLE 95. HRMS calculated for $C_{30}H_{28}F_5N_3O_3S_2$: 637.1492: found 638.1559 [(M+H)$^+$ form].

3-[[4-hydroxy-1-[trans-2-(1,2,4-triazol-1-yl)cyclohexanecarbonyl]-4-piperidyl]methyl]-7-phenyl-thieno[3,4-d]pyrimidin-4-one (Example 96)

Using Step 3 of General Procedure 3 starting from Preparation R3h and trans-2-(1,2,4-triazol-1-yl)cyclohexanecarboxylic acid as reagents, the corresponding halogenated compound was obtained which, using General Procedure 5, was reacted with phenylboronic acid to give EXAMPLE 96. HRMS calculated for $C_{27}H_{30}N_6O_3S$: 518.21: found 519.2173 [(M+H)$^+$ form].

3-[[4-hydroxy-1-[cis-2-(1,2,4-triazol-1-yl)cyclohexanecarbonyl]-4-piperidyl]methyl]-7-phenyl-thieno[3,4-d]pyrimidin-4-one (Example 97)

Using Step 3 of General Procedure 3 starting from Preparation R3 and cis-2-0,2,4-triazol-1-yl)cyclohexanecarboxylic acid as reagents, the corresponding halogenated compound was obtained which, using General Procedure 5, was reacted with phenylboronic acid to give EXAMPLE 97. HRMS calculated for $C_{27}H_{30}N_6O_3S$: 518.21: found 519.2170 [(M+H)$^+$ form].

3-[[1-(trans-4,4-dimethyl-2-phenyl-cyclohexanecarbonyl)-4-hydroxy-4-piperidyl]methyl]-7-phenyl-thieno[3,4-d]pyrimidin-4-one, enantiomer 1 (Example 9g)

and

3-[[1-(trans-4,4-dimethyl-2-phenyl-cyclohexanecarbonyl)-4-hydroxy-4-piperidyl]methyl]-7-phenyl-thieno[3,4-d]pyrimidin-4-one, enantiomer 2 (Example 99)

Using Step 3 of General Procedure 3 starting from Preparation R3h and trans-4,4-dimethyl-2-phenyl-cyclohexanecarboxylic acid as reagents, the corresponding halogenated compound was obtained which, using General Procedure 5, was reacted with phenylboronic acid to give EXAMPLE 98 and EXAMPLE 99 separately by chiral chromatography.
EXAMPLE 9g: HRMS calculated for $C_{33}H_{37}N_3O_3S$: 555.2556: found 556.2628 [(M+H)$^+$ form].
EXAMPLE 99: HRMS calculated for $C_{33}H_{37}N_3O_3S$: 555.2556: found 556.26149 [(M+H)$^+$ form].

6-amino-3-[[4-hydroxy-1-(trans-2-phenylcyclohexanecarbonyl)-4-piperidyl]methyl]pyrido[3,2-d]pyrimidin-4-one (Example 100)

EXAMPLE 94 was dissolved in TFA and heated and stirred at 70° C. for 2 hours, then it was evaporated. The residue was purified by preparative HPLC (on C-18 Gemini-NX 5 μm column, 5 mM aqueous $NH_4HCO_3$-MeCN, gradient) to give EXAMPLE 100. HRMS calculated for $C_{26}H_{31}N_5O_3$: 461.2427: found 462.2513 [(M+H)$^+$ form].

N-[3-[[4-hydroxy-1-(trans-2-phenylcyclohexanecarbonyl)-4-piperidyl]methyl]-4-oxo-pyrido[3,2-d]pyrimidin-6-yl]tetrahydrofuran-3-carboxamide (Example 101)

Using General Procedure 6 and starting from EXAMPLE 100 and tetrahydrofuran-3-carboxylic acid as reagents. EXAMPLE 101 was obtained. HRMS calculated for $C_{31}H_{37}N_5O_5$: 559.2795: found 560.2874 [(M+H)$^+$ form].

N-[3-[[4-hydroxy-1-(trans-2-phenylcyclohexanecarbonyl)-4-piperidyl]methyl]-4-oxo-pyrido[3,2-d]pyrimidin-6-yl]-2-(2-oxoindolin-6-yl)acetamide (Example 102)

Using General Procedure 6 and starting from EXAMPLE 100 and 2-(2-oxoindolin-6-yl)acetic acid as reagents. EXAMPLE 102 was obtained. HRMS calculated for $C_{36}H_{38}N_6O_5$: 634.2903: found 635.299 (M+H)$^+$ form.

2-hydroxy-N-[3-[[4-hydroxy-1-(trans-2-phenylcyclohexanecarbonyl)-4-piperidyl]methyl]4-oxo-pyrido[3,2-d]pyrimidin-6-yl]cyclopentanecarboxamide (Example 103)

Using General Procedure 6 and starting from EXAMPLE 100 and 2-hydroxycyclopentane-1-carboxylic acid as reagents EXAMPLE 103 was obtained as mixture of diastereomers. HRMS calculated for $C_{32}H_{39}N_5O_5$: 573.2951: found 574.3039 and 574.3043 [(M+H)$^+$ form].

2-(3-hydroxyphenyl)-N-[3-[[4-hydroxy-1-(trans-2-phenylcyclohexanecarbonyl)-4-piperidyl]methyl]-4-oxo-pyrido[3,2-d]pyrimidin-6-yl]acetamide (Example 104)

Using General Procedure 6 and starting from EXAMPLE 100 and 3-hydroxyphenylacetic acid as reagents, EXAMPLE 104 was obtained. HRMS calculated for $C_{34}H_{37}N_5O_5$: 595.2795: found 96.2873 [(M+H)$^+$ form].

2-(5-hydroxy-1H-idol-3-yl)-N-[3-[[4-hydroxy-1-(trans-2-phenylcyclohexanecarbonyl)-4-piperidyl]methyl]-4-oxo-pyrido[3,2-d]pyrimidin-6-yl]acetamide (Example 105)

Using General Procedure 6 and starting from EXAMPLE 100 and 5-hydroxyindole-3-acetic acid as reagents. EXAMPLE 145 was obtained. HRMS calculated for $C_{36}H_{38}N_6O_5$: 634.2903: found 635.2982 [(M+H)$^+$ form].

N-[3-[[4-hydroxy-1-(trans-2-phenylcyclohexanecarbonyl)-4-piperidyl]methyl]-4-oxo-pyrido[3,2-d]pyrimidin-6-yl]-2-tetrahydrofuran-2-yl-acetamide (Example 106)

Using General Procedure 6 and starting from EXAMPLE 100 and 2-(oxolan-2-yl)acetic acid as reagents. EXAMPLE 106 was obtained. HRMS calculated for $C_{32}H_{39}N_5O_5$: 573.2951: found 574.302 [(M+H)$^+$ form].

N-[3-[[4-hydroxy-1-(trans-2-phenylcyclohexanecarbonyl)-4-piperidyl]methyl]-4-oxo-pyrido[3,2-d]pyrimidin-6-yl]-4-methoxy-benzamide (Example 107)

Using General Procedure 6 and starting from EXAMPLE 100 and p-anisic acid as reagents, EXAMPLE 107 was obtained. HRMS calculated for $C_{34}H_{37}N_5O5$: 595.2795: found 596.2875 [(M+H)$^+$ form].

3-(2-amino-2-oxo-ethyl)sulfanyl-N-[3-[[4-hydroxy-1-(trans-2-phenylcyclohexanecarbonyl)-4-piperidyl]methyl]-4-oxo-pyrido[3,2-d]pyrimidin-6-yl]propanamide (Example 108)

Using General Procedure 6 and starting from EXAMPLE 100 and 3-[(2-amino-2-oxoethyl)thio]propanoic acid as reagents, EXAMPLE 100 was obtained. HRMS calculated for $C_{31}H_{38}N_5O_5S$: 606.2625: found 607.2704 [(M+H)$^+$ form].

3-[[4-hydroxy-1-(trans-2-phenylcyclohexanecarbonyl)-4-piperidyl]methyl]-7-(3-pyridylmethyl)pyrrolo[2,3-d]pyrimidin-4-one (Example 109)

EXAMPLE 92 was dissolved in abs. DMF and 3-(bromomethyl)pyridine (1.5eq.) and $Cs_2CO_3$ (3 eq.) were added. The solution was heated and stirred for 116 hours, then it was purified by preparative HPLC (on C-18 Gemini-NX 5 μm column, 0.2% HCOOH aqueous solution-MeCN, gradient) to give EXAMPLE 109. HRMS calculated for $C_{31}H_{35}N_5O_3$: 525.274: found 526.2919 [(M+H)$^+$ form].

3-[[4-hydroxy-1-(trans-2-phenylcyclohexanecarbonyl)-4-piperidyl]methyl]-7-(3-thienylmethyl)pyrrolo[2,3-d]pyrimidin-4-one (Example 110)

EXAMPLE 92 was dissolved in abs. DMF and 3-(bromomethyl)thiophene (1.5 eq.) and $Cs_2CO_3$ (3 eq.) were added. The solution was heated and stirred for 116 hours, then it was purified by preparative HPLC (on C-18 Gemini-NX 5 μm column, 5 mM aqueous $NH_4HCO_3$-MeCN, gradient) to give EXAMPLE 110. HRMS calculated for $C_{30}H_{34}N_4O_3S$: 530.2352: found 531.2433 [(M+H)$^+$ form].

3-[[1-[trans-4,4-difluoro-2-phenyl-cyclohexanecarbonyl]-4-hydroxy-4-piperidyl]methyl]-7-methyl-pyrrolo[2,3-d]pyrimidin-4-one, enantiomer 1 (Example 111)

and

3-[[1-[trans-4,4-difluoro-2-phenyl-cyclohexanecarbonyl]-4-hydroxy-4-piperidyl]methyl]-7-methyl-pyrrolo[2,3-d]pyrimidin-4-one, enantiomer 1 (Example 112)

Using General Procedure 3 and starting from 7-methyl-3H-pyrrolo[2,3-d]pyrimidin-4-one and Preparation R1d as reagents. EXAMPLE 111 and EXAMPLE 112 were obtained separately by chiral chromatography.

EXAMPLE 111: HRMS calculated for $C_{26}H_{30}F_2N_4O_3$: 494.2296: found 485.2352 [(M+H)$^+$ form].

EXAMPLE 112: HRMS calculated for $C_{26}H_{30}F_2N_4O_3$: 494.2286: found 485.2354 [(M+H)$^+$ form].

3-[[1-[trans-4,4-difluoro-2-phenyl-cyclohexanecarbonyl]-4-hydroxy-4-piperidyl]methyl]-7-isopropyl-pyrrolo[2,3-d]pyrimidin-4-one, enantiomer 1 (Example 113)

and

3-[[1-[trans-4,4-difluoro-2-phenyl-cyclohexanecarbonyl]4-hydroxy-4-piperidyl]methyl]-7-isopropyl-pyrrolo[2,3-d]pyrimidin-4-one, enantiomer 2 (Example 114)

Using General Procedure 8 and starting from Preparation R2o and Preparation R1d as reagents. EXAMPLE 113 and EXAMPLE 114 were obtained separately by chiral chromatography.

EXAMPLE 113: HRMS calculated for $C_{28}H_{34}F_2N_4O_3$: 512.2599: found 513.2683 [(M+H)$^+$ form].

EXAMPLE 114: HRMS calculated for $C_{28}H_{34}F_2N_4O_3$: 512.2599; round 513.2658 [(M+H)$^+$ form].

7-cyclopropyl-3-[[1-[trans-4,4-difluoro-2-phenyl-cyclohexanecarbonyl]-4-hydroxy-4-piperidyl]methyl]pyrrolo[2,3-d]pyrimidin-4-one, enantiomer 1 (Example 115)

and 7-cyclopropyl-3-[[1-[trans-4,4-difluoro-2-phenyl-cyclohexanecarbonyl]-4-hydroxy-4-piperidyl]methyl]pyrrolo[2,3-d]pyrimidin-4-one, enantiomer 2 (Example 116)

Using General Procedure 8 starting from Preparation R2p and Preparation R1d as reagents. EXAMPLE 115 and EXAMPLE 116 were obtained separately by chiral chromatography.

EXAMPLE 115: HRMS calculated for $C_{28}H_{32}F_2N_4O_3$: 510.2442: found 51.2514 [(M+H)$^+$ form].

EXAMPLE 116: HRMS calculated for $C_{28}H_{32}F_2N_4O_3$: 510.2442: found 511.2509 [(M+H)$^+$ form].

3-{[4-hydroxy-1-trans-1-methyl-6-oxo-2-phenylpiperidine-3-carbonyl)piperidin-4-yl]methyl}-7-(4-methoxyphenyl)-3,7-dihydro-4H-pyrrolo[2,3-d]pyrimidin-4-one, enantiomer 1 (Example 117)

and

3-{[4-hydroxy-1-(trans-1-methyl-6-oxo-2-phenylpiperidine-3-carbonyl)piperidin-4-yl]methyl}-7-(4-methoxyphenyl)-3,7-dihydro-4H-pyrrolo[2,3-d]pyrimidin-4-one, enantiomer 2 (Example 318)

Using General Procedure 6 starting from Preparation R3b and trans-1-methyl-6-oxo-2-phenyl-piperidine-3-carboxylic acid as reagents. EXAMPLE 117 and EXAMPLE 118 were obtained separately by chiral chromatography.

EXAMPLE 117: HRMS calculated for $C_{31}H_{33}N_5O_4$: 569.2638: found 570.2717 [(M+H)$^+$ form].

EXAMPLE 118: HRMS calculated for $C_{31}H_{33}N_5O_4$: 569.2639: found 570.2721 [(M+H)$^+$ form].

Pharmacological Study

Example A: Evaluation of the Inhibition of USP7 by the Fluorescence Intensity (FLINT) Readings USP7 activity was measured using Rhodamine-110 c-terminal labelled Ubiquitin as a substrate (Viva Biosciences). Incubation with USP7 results in the release of Rhodamine-110 leading to an increase in fluorescence which can be used in the continuous measurement of USP7 activity.

The USP7 reactions were performed in a 50 μL volume, in 384 well black solid low binding plates (Corning #3575). The reaction buffer consisted of 100 mM Bicine pH 8.0, 0.01% TritonX 100, 1 mM TCEP, and 10% DMSO.

0.25 nM His-His-USP7 (aa208-560, [C315A]) was incubated with compound (final concentration 10% DMSO) for 60 minutes at 30° C. The reaction was then initiated by the addition of 500 nM Ubiquitin-Rhodamine-10 substrate and the plate read every 3 minutes for 21 minutes to measure the release of Rhodamine-110. Fluorescence Intensity (FLINT) readings were measured using a Biomek Neo plate reader (Ex. 485 nm. Em. 535 nm).

The inhibition of increasing doses of compound was expressed as a percentage reduction in kinetic rate compared to the kinetic rates established between 'DMSO only' and 'total inhibition' controls (no USP7). The inhibitory concentrations that gave a 50% reduction in kinetic rate (IC$_{50}$) were determined, from 11-point dose response curves, in XL-Fit using a 4-Parameter Logistic Model (Sigmoidal Dose-Response Model).

The results presented in Table I below show that compounds of the invention inhibit interaction between USP7 protein and the fluorescent peptide described hereinbefore.

Example B: In Vitro Cytotoxicity

The cytotoxicity studies were evaluated by MTT assay and carried out on MM 1S multiple myeloma or Z138 mantle cell lymphoma tumour cell lines. The cells are distributed onto microplates and exposed to the test compounds for 96 hours. The cell viability is then quantified by a colorimetric assay, the Microculture Tetrazolium Assay (Carmichael et. al., *Cancer Res.* 1997, 47, 936-942). The results are expressed in IC$_{50}$ (the concentration of compound that inhibits cell viability by 50%) and are presented in Table I below. The results show that the compounds of the invention are cytotoxic.

TABLE 1

| IC$_{50}$ of USP7 inhibition and of cytotoxicity for MM1S cells | | |
| --- | --- | --- |
| EXAMPLE | IC$_{50}$ (M) USP7 FLINT | IC50 (M) MTT |
| 1 | 9.16E-07 | NT |
| 2 | 4.39E-07 | NT |
| 3 | 5.30E-07 | NT |
| 4 | 4.58E-06 | NT |
| 5 | 1.94E-05 | NT |
| 6 | 2.80E-05 | NT |
| 7 | 6.50E-06 | NT |
| 8 | 1.33E-05 | NT |
| 9 | 3.59E-08 | 1.39E-08 |
| 10 | 4.25E-07 | NT |
| 11 | 2.57E-06 | NT |
| 12 | 7.11E-08 | 3.45E-08 |
| 13 | 1.11E-05 | NT |
| 14 | 2.71E-08 | 6.42E-09/1.47E-08 |
| 15 | 2.61E-08 | 8.76E-09 |
| 16 | 2.97E-06 | NT |
| 17 | 3.35E-08 | 4.21E-09 |
| 18 | 5.06E-08 | 6.36E-07 |
| 19 | 1.43E-08 | 1.95E-07 |
| 20 | 2.93E-08 | 2.10E-07 |
| 21 | 2.69E-08 | 3.40E-09 |
| 22 | 3.16E-08 | 9.88E-09 |
| 23 | 1.72E-08 | 7.01E-08 |
| 24 | 2.17E-07 | 1.46E-07 |
| 26 | 6.70E-08 | NT |

TABLE 1-continued

IC$_{50}$ of USP7 inhibition and of cytotoxicity for MM1S cells

| EXAMPLE | IC$_{50}$ (M) USP7 FLINT | IC50 (M) MTT |
|---|---|---|
| 27 | 3.15E−08 | 4.65E−08 |
| 29 | 6.12E−07 | NT |
| 30 | 1.59E−08 | 1.08E−08 |
| 31 | 2.76E−06 | NT |
| 32 | 3.53E−08 | 1.58E−08 |
| 33 | 4.67E−06 | NT |
| 34 | 2.31E−08 | 2.45E−08/5.66E−09 |
| 35 | 1.35E−05 | NT |
| 36 | 7.53E−08 | 1.26E−07 |
| 37 | 4.63E−08 | 8.41E−08 |
| 38 | 3.99E−07 | NT |
| 40 | 8.83E−07 | NT |
| 41 | 1.30E−08 | 7.22E−09 |
| 42 | 1.59E−06 | NT |
| 43 | 9.81E−09 | 3.23E−08 |
| 44 | 2.75E−06 | NT |
| 45 | 8.60E−08 | NT |
| 46 | 6.85E−07 | NT |
| 48 | 4.13E−07 | NT |
| 50 | 5.70E−07 | NT |
| 51 | 1.01E−05 | NT |
| 52 | 7.18E−08 | 1.00E−07 |
| 55 | 1.13E−07 | NT |
| 56 | 2.55E−06 | NT |
| 57 | 2.84E−05 | NT |
| 58 | 2.03E−05 | NT |
| 59 | 6.52E−08 | NT |
| 60 | 7.25E−07 | NT |
| 61 | 7.23E−08 | NT |
| 62 | 6.82E−07 | NT |
| 69 | 1.05E−05 | NT |
| 70 | 9.23E−06 | NT |
| 71 | 1.62E−07 | NT |
| 73 | 8.38E−08 | NT |
| 74 | 2.90E−06 | NT |
| 75 | 5.91E−08 | 3.29E−09 |
| 76 | 6.64E−06 | NT |
| 77 | 5.91E−07 | NT |
| 78 | 1.03E−05 | NT |
| 79 | 6.01E−08 | NT |
| 81 | 7.63E−05 | NT |
| 82 | 1.01E−05 | NT |
| 83 | 6.32E−07 | NT |
| 84 | 6.11E−07 | NT |
| 86 | 1.25E−07 | NT |
| 88 | 3.10E−07 | NT |
| 90 | 2.92E−06 | NT |
| 91 | 1.37E−07 | NT |
| 92 | 1.24E−07 | 5.23E−07 |
| 93 | 1.71E−07 | NT |
| 94 | 3.51E−07 | NT |
| 99 | 2.68E−07 | NT |
| 100 | 2.26E−07 | NT |
| 101 | 9.96E−08 | NT |
| 102 | 1.58E−08 | 5.39E−06 |
| 103 | 1.25E−07 | NT |
| 104 | 2.17E−08 | NT |
| 105 | 1.53E−08 | NT |
| 106 | 1.00E−07 | NT |
| 107 | 1.02E−07 | NT |
| 108 | 7.65E−08 | NT |
| 109 | 1.01E−06 | NT |
| 110 | 4.50E−07 | NT |
| 112 | 4.71E−07 | NT |
| 113 | 4.56E−07 | NT |
| 116 | 2.05E−07 | NT |
| 117 | 3.09E−08 | 2.64E−08 |
| 118 | 4.64E−06 | NT |

Note:
IC$_{50}$ of cytotoxicity for Z138 tumour cell line are underlined.
NT: not tested Example C: Anti-Tumor Activity In Vivo The anti-tumour activity of the compounds of the invention is evaluated in a xenograft model of multiple myeloma and/or acute lymphoblastic leukaemia cells.

Human tumour cells are grafted subcutaneously into immunosuppressed mice.

When the tumour volume (TV) reaches about 200 mm$^3$, the mice are treated per os with the various compounds once a day for 5 days on/2 days off during 3 weeks. The tumour mass is measured twice weekly from the start of treatment.

The compounds of the invention display anti-tumour activities represented by the TGI (tumor growth inhibition) at the end of the treatment period. The TGI is defined as follows:

$$TGI = \left(1 - \frac{\text{Median } (DTV \text{ at } Dx \text{ in treated group})}{\text{Median } (DTV \text{ at } Dx \text{ in control group})}\right) \times 100.$$

with:
DTV (delta tumoral volume) at Dx=(TV at Dx)−(TV at randomization for each animal).

Example D: Pharmaceutical Composition: Tablets

| 1000 tablets containing a dose of 5 mg of a compound selected from Examples 1 to 118 | 5 g |
|---|---|
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:
1. A compound of formula (I):

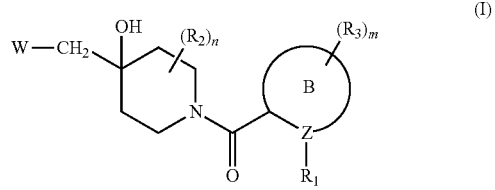

or a pharmaceutically acceptable salt or stereoisomer thereof,
wherein:
W represents:

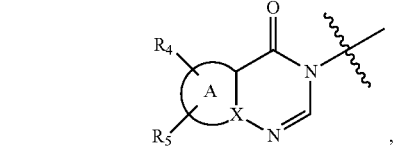

wherein:
ring A represents heteroaryl, wherein the heteroaryl is optionally substituted with 1, 2, 3, or 4 substituents independently selected from the group consisting of halogen, cyano, nitro, N-oxide, oxo, (C$_1$-C$_6$) alkyl, ($C_1$-$C_6$) haloalkyl, ($C_2$-$C_6$) alkenyl, ($C_2$-$C_6$) alkynyl, C(O)R', C(O)NR'R", C(O)OR', OC(O)R', $Y_1$—NR'R", $Y_1$—NR'—C(O)—R", $Y_1$—NR'—C(O)—OR", $Y_1$—OR', $Y_1$—S(O)$_m$—R', cyclopropyl, and pyridinyl, and further wherein the pyridinyl substituent is optionally substituted with a ($C_1$-$C_6$) alkyl substituent;

$R_4$ represents hydrogen, halogen, oxo, ($C_1$-$C_6$) alkyl, ($C_1$-$C_6$) haloalkyl, ($C_2$-$C_6$) alkenyl, ($C_2$-$C_6$) alkynyl, $Y_1$—$NR_6R_7$, $Y_1$—$NR_6$—C(O)—$R_7$, $Y_1$—$OR_6$, $Y_1$-$Cy_1$, $Cy_1$—$R_7$, or $Cy_1$—ORS;

$R_5$ represents hydrogen, halogen, cyano, ($C_1$-$C_6$) alkyl, or ($C_1$-$C_6$) hydroxyalkyl;

$R_6$ represents hydrogen or ($C_1$-$C_6$) alkyl;

$R_7$ represents hydrogen, ($C_1$-$C_6$) alkyl, $Y_2$—$SR_8$, or $Y_2$-$Cy_2$;

$R_8$ represents hydrogen or ($C_1$-$C_6$) alkyl;

X represents C, CH, or N;

$Y_1$ represents a bond or ($C_1$-$C_4$) alkylene;

$Y_2$ represents a bond or ($C_1$-$C_4$) alkylene;

$Cy_1$ represents cycloalkyl, heterocycloalkyl, aryl, or heteroaryl, wherein the cycloalkyl, heterocycloalkyl, aryl, and heteroaryl are each optionally substituted with 1, 2, 3, or 4 substituents independently selected from the group consisting of halogen, cyano, nitro, N-oxide, oxo, ($C_1$-$C_6$) alkyl, ($C_1$-$C_6$) haloalkyl, ($C_2$-$C_6$) alkenyl, ($C_2$-$C_6$) alkynyl, C(O)R', C(O)NR'R", C(O)OR', OC(O)R', $Y_1$—NR'R", $Y_1$—NR'—C(O)—R", $Y_1$—NR'—C(O)—OR", $Y_1$—OR', $Y_1$—S(O)$_m$—R', cyclopropyl, and pyridinyl, and further wherein the pyridinyl substituent is optionally substituted with a ($C_1$-$C_6$) alkyl substituent; and $Cy_2$ represents cycloalkyl, heterocycloalkyl, aryl, or heteroaryl, wherein the cycloalkyl, heterocycloalkyl, aryl, and heteroaryl are each optionally substituted with 1, 2, 3, or 4 substituents independently selected from the group consisting of halogen, cyano, nitro, N-oxide, oxo, ($C_1$-$C_6$) alkyl, ($C_1$-$C_6$) haloalkyl, ($C_2$-$C_6$) alkenyl, ($C_2$-$C_6$) alkynyl, C(O)R', C(O)NR'R", C(O)OR', OC(O)R', $Y_1$—NR'R", $Y_1$—NR'—C(O)—R", $Y_1$—NR'—C(O)—OR", $Y_1$—OR', $Y_1$—S(O)$_m$ —R', cyclopropyl, and pyridinyl, and further wherein the pyridinyl substituent is optionally substituted with a ($C_1$-$C_6$) alkyl substituent;

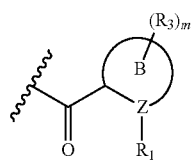

represents:

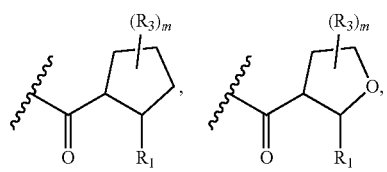

-continued

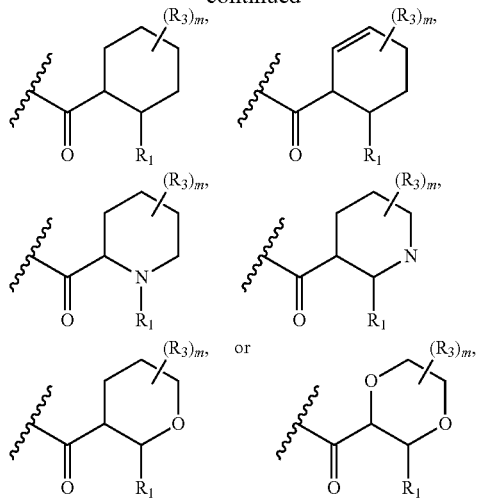

wherein:

$R_1$ represents cycloalkyl, heterocycloalkyl, aryl, or heteroaryl, wherein the cycloalkyl, heterocycloalkyl, aryl, and heteroaryl are each optionally substituted with 1, 2, 3, or 4 substituents independently selected from the group consisting of halogen, cyano, nitro, N-oxide, oxo, ($C_1$-$C_6$) alkyl, ($C_1$-$C_6$) haloalkyl, ($C_2$-$C_6$) alkenyl, ($C_2$-$C_6$) alkynyl, C(O)R', C(O)NR'R", C(O)OR', OC(O)R', $Y_1$—NR'R", $Y_1$—NR'—C(O)—R", $Y_1$—NR'—C(O)—OR", $Y_1$—OR', $Y_1$—S(O)$_m$—R', cyclopropyl, and pyridinyl, and further wherein the pyridinyl substituent is optionally substituted with a ($C_1$-$C_6$) alkyl substituent;

each $R_3$ independently represents hydrogen, halogen, oxo, ($C_1$-$C_6$) alkyl, or OH; and m represents 0, 1, or 2;

each $R_2$ independently represents hydrogen or halogen;

each R' independently represents hydrogen, ($C_1$-$C_6$) alkyl, ($C_1$-$C_6$) haloalkyl, ($C_1$-$C_6$) hydroxyalkyl, ($C_1$-$C_6$) alkyl—O($C_1$-$C_6$) alkyl, $CH_2$-cyclopropyl, ($C_2$-$C_6$) alkenyl, O(Ci-$C_6$) alkyl, tetrahydropyranyl, or phenyl;

each R" independently represents hydrogen, ($C_1$-$C_6$) alkyl, ($C_1$-$C_6$) haloalkyl, ($C_1$-$C_6$) hydroxyalkyl, ($C_1$-$C_6$) alkyl—O($C_1$-$C_6$) alkyl, $CH_2$-cyclopropyl, ($C_2$-$C_6$) alkenyl, O($C_1$-$C_6$) alkyl, tetrahydropyranyl, or phenyl; or each R' and R", together with the nitrogen atom to which they are attached, independently forms a non-aromatic ring having 5, 6, or 7 ring members, wherein each non-aromatic ring optionally and independently contains one additional heteroatom or heteroatomic group selected from the group consisting of N, NH, N($C_1$-$C_6$) alkyl, $N^+$[($C_1$-$C_6$) alkyl]$_2$, and O; and n represents 0, 1, or 2;

wherein cycloalkyl represents a non-aromatic, monocyclic, or fused bicyclic carbocyclic ring having 3, 4, 5, 6, or 7 ring members;

wherein heterocycloalkyl represents a non-aromatic, monocyclic, or fused bicyclic ring having 3, 4, 5, 6, 7, 8, 9, or 10 ring members, and further having 1, 2, or 3 heteroatoms or heteroatomic groups independently selected from the group consisting of N, NH, O, and S;

wherein aryl represents phenyl, naphthyl, or indanyl; and wherein heteroaryl represents a monocyclic or fused bicyclic ring having at least one aromatic moiety and further having 5, 6, 7, 8, 9, or 10 ring members and 1, 2, or 3 heteroatoms independently selected from the group consisting of N, O, and S.

2. The compound according to claim 1, or a pharmaceutically acceptable salt or stereoisomer thereof, wherein W represents:

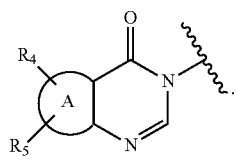

3. The compound according to claim 1, or a pharmaceutically acceptable salt or stereoisomer thereof, wherein $R_1$ represents pyrrolidinyl, phenyl, pyrrolyl, furyl, thienyl, pyrazolyl, imidazolyl, oxazolyl, thiazolyl, triazolyl, or pyridinyl.

4. The compound according to claim 1, or a pharmaceutically acceptable salt or stereoisomer thereof, wherein each $R_2$ independently represents hydrogen or fluoro.

5. The compound according to claim 1, or a pharmaceutically acceptable salt or stereoisomer thereof, wherein each $R_3$ independently represents hydrogen, fluoro, oxo, $CH_3$, or OH.

6. The compound according to claim 1, or a pharmaceutically acceptable salt or stereoisomer thereof, wherein $R_4$ represents hydrogen, halogen, $(C_1-C_6)$ alkyl, $Y_1$—$NR_6R_7$, $Y_1$—$NR_6$—$C(O)$—$R_7$, or $Y_1$-$Cy_1$.

7. The compound according to claim 1, or a pharmaceutically acceptable salt or stereoisomer thereof, wherein:
    $R_5$ represents hydrogen; and
    $R_6$ represents hydrogen.

8. The compound according to claim 1, or a pharmaceutically acceptable salt or stereoisomer thereof, wherein $R_7$ represents hydrogen, $Y_2$—$SR_8$, or $Y_2$-$Cy_2$.

9. The compound according to claim 1, wherein the compound, or stereoisomer thereof, is selected from the group consisting of:

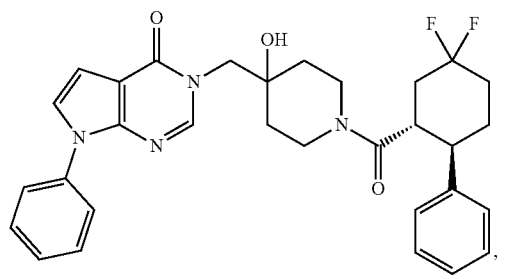

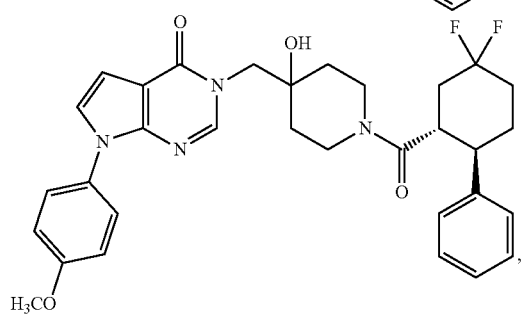

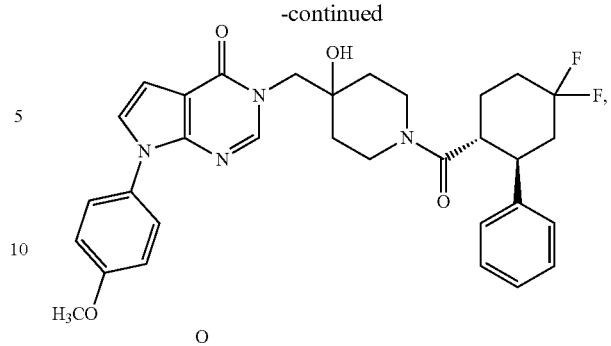

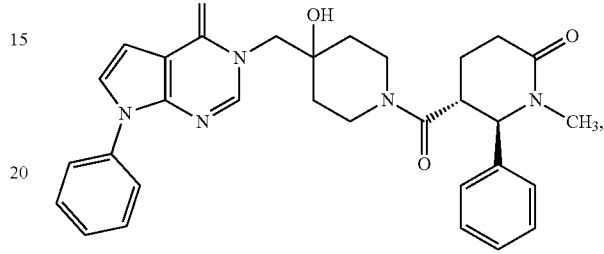

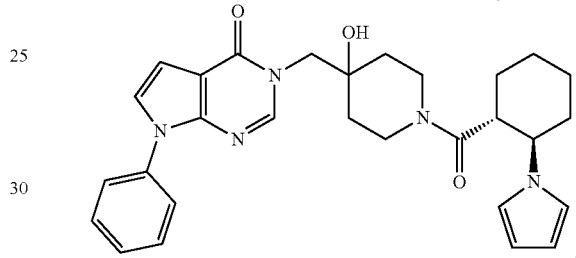

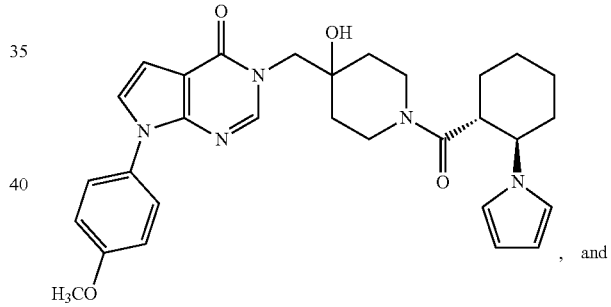

, and

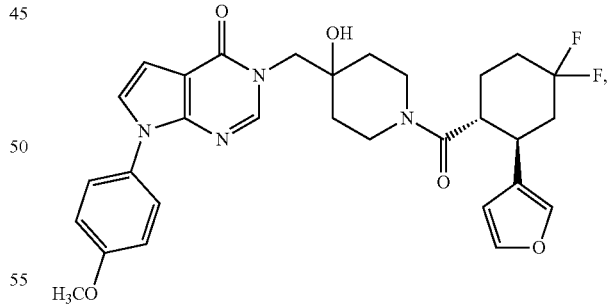

or a pharmaceutically acceptable salt thereof.

10. A pharmaceutical composition comprising one or more pharmaceutically acceptable excipients together with the compound according to claim 1, or a pharmaceutically acceptable salt or stereoisomer thereof.

11. A combination comprising the compound according to claim 1, or a pharmaceutically acceptable salt or stereoisomer thereof, and an anticancer agent;
    wherein the anticancer agent is selected from the group consisting of an antibody, an anti-metabolite, a chimeric antigen receptor T-cell therapy, an E3 ligase inhibitor, a genotoxic agent, an immunomodulator, a kinase inhibitor, a mitotic poison, a proteasome inhibitor, and a protein-protein interaction inhibitor.

12. A pharmaceutical composition comprising one or more pharmaceutically acceptable excipients together with the combination according to claim 11.

* * * * *

UNITED STATES PATENT AND TRADEMARK OFFICE
CERTIFICATE OF CORRECTION

PATENT NO. : 11,332,472 B2
APPLICATION NO. : 16/764982
DATED : May 17, 2022
INVENTOR(S) : András Kotschy et al.

It is certified that error appears in the above-identified patent and that said Letters Patent is hereby corrected as shown below:

In the Claims

Claim 1, Column 51, Line 12:
OR5 should read $OR_7$.

Signed and Sealed this
Nineteenth Day of July, 2022

Katherine Kelly Vidal
*Director of the United States Patent and Trademark Office*